(12) United States Patent
Griffiths

(10) Patent No.: US 6,808,874 B2
(45) Date of Patent: Oct. 26, 2004

(54) METHODS OF MONITORING ENZYME ACTIVITY

(75) Inventor: Gary Griffiths, Oldham (GB)

(73) Assignee: Cyclacel Ltd., London (GB)

( * ) Notice: Subject to any disclaimer, the term of this patent is extended or adjusted under 35 U.S.C. 154(b) by 423 days.

(21) Appl. No.: 09/877,919

(22) Filed: Jun. 7, 2001

(65) Prior Publication Data

US 2002/0019002 A1 Feb. 14, 2002

Related U.S. Application Data

(60) Provisional application No. 60/211,313, filed on Jun. 13, 2000.

(51) Int. Cl.[7] ................................................ C12Q 1/00
(52) U.S. Cl. ........................ 435/4; 435/7.1; 435/15; 435/24
(58) Field of Search ..................... 435/4, 6, 7.1, 7.6, 435/15, 24

(56) References Cited

U.S. PATENT DOCUMENTS

2002/0197606 A1 * 12/2002 Craig .......................... 435/6

FOREIGN PATENT DOCUMENTS

| WO | WO92/00388 | 1/1992 | ............ C12Q/1/68 |
|----|------------|--------|-----------------------|
| WO | WO97/28261 | 8/1997 | ............ C12N/15/12 |
| WO | WO98/06737 | 2/1998 | ............ C07H/12/04 |
| WO | WO 99/11774 | * 3/1998 | |
| WO | WO98/18956 | 5/1998 | ............ C12Q/1/42 |
| WO | WO99/11774 | 3/1999 | ............ C12N/15/09 |
| WO | WO99/13338 | 3/1999 | ............ G01N/33/68 |
| WO | WO00/50630 | 8/2000 | ............ C12Q/1/00 |
| WO | WO 00/50631 | * 8/2000 | |
| WO | WO00/50631 | 8/2000 | ............ C12Q/1/00 |
| WO | WO00/50896 | 8/2000 | ......... G01N/33/542 |

OTHER PUBLICATIONS

Wang Y. In r as d and alt red DNA Binding of Human p53 by S and G2/M. Nautre vol. 376, pp. 89–91, 1995.*
Bullock B. Phosphorylation of the cAMP Response Element Binding Protein CREB . . . Biochemistry 37, 3795–3809, 1998.*

Bullock and Habener "Phosphorylation of the CAMP Response Element Binding Protein CREB by CAMP–Dependent Protein Kinase A and Glycogen Synthase Kinase–3 Alters DNA–Binding Affinity, Conformation, and Increases Net Charge" *Biochemistry* 1998, V. 37, 3795–3809.

Wang and Prives "Increased and altered DNA binding of human p53 by S and G2/M but not G1 cyclin–dependent kinases" *Nature*, V. 376, Jul. 6, 1995.

Huang, et al. "Phosphorylation stimulates the cooperative DNA–binding properties of the transcription factor OmpR" *Proc. Natl. Acad. Sci. USA*, V. 94, p. 2828–2832, Apr. 1997.

Fouts, et al. "Site–Specific Phosphorylation of the Human Immunodeficiency Virus Type–1 Rev Protein Accelerates Formation of an Efficient RNA–Binding Conformation" *Biochemistry*1997, V. 36, p. 13256–13262.

Copy of the International Search Report (PCT/GB01/02502).

Momparler & Bovenzi,DNA Methylation and Cancer, *Journal of Cellular Physiology*, 183:145–154 (2000).

Robertson & Jones "DNA methylation: past, present and future directions", *Carcinogenesis*, V. 21 No. 3 pp461–467 (2000).

Honda, et al. "Oncoprotein MDM2 is a ubiquitin ligase E3 for tumor suppressor p53", *FEBS Lett.*, V. 420 pp 25–27 (1997).

* cited by examiner

*Primary Examiner*—Ralph Gitomer
(74) *Attorney, Agent, or Firm*—Palmer & Dodge LLP; Kathleen M. Williams

(57) ABSTRACT

We describe a method for monitoring the activity of an enzyme, the method comprising the steps of: providing a binding domain which includes a site for enzymatic modification; providing a binding partner which binds to the binding domain in a manner which is dependent upon modification of the site. The binding domain is contacted with the enzyme; and binding of the binding domain to the binding partner is detected as an indication of the activity of the enzyme. One of the binding domain and binding partner comprises a polypeptide and the other of the binding domain and binding partner comprises a nucleic acid.

60 Claims, No Drawings

METHODS OF MONITORING ENZYME ACTIVITY

This application claims benefit to provisional application No. 60/211,313 filed Jun. 13, 2000.

FIELD OF THE INVENTION

The invention relates to monitoring of enzyme activities, in particular, activities of enzymes which cause modification of proteins or nucleic acids.

BACKGROUND OF THE INVENTION

Enzymatic modification of proteins has been known for over 40 years and since then has become a ubiquitous feature of protein structure. The addition of biochemical groups to translated polypeptides has wide-ranging effects on protein stability, protein secondary/tertiary structure, enzyme activity and in more general terms on the regulated homeostasis of cells. Such modifications include, but are not limited to, the addition of a phosphate (phosphorylation), carbohydrate (glycosylation), ADP-ribosyl (ADP ribosylation), fatty acid (prenylation, which includes but is not limited to: myristoylation and palmitylation), ubiquitin (ubiquitination) and sentrin (sentrinization; a ubiquitination-like protein modification). Additional examples of enzymatic modification include methylation, acetylation, hydroxylation, iodination and flavin linkage. Many of the identified modifications have important consequences for the activity of those polypeptides so modified.

Phosphorylation is a well-studied example of an enzymatic modification of a protein. There are many cases in which polypeptides form higher order tertiary structures with like polypeptides (homo-oligomers) or with unlike polypeptides (hetero-oligomers). In the simplest scenario, two identical polypeptides associate to form an active homodimer. An example of this type of association is the natural association of myosin H molecules in the assembly of myosin into filaments.

The dimerization of myosin II monomers is the initial step in seeding myosin filaments. The initial dimerization is regulated by phosphorylation the effect of which is to induce a conformational change in myosin II secondary structure resulting in the folded 10S monomer subunit extending to a 6S molecule. This active molecule is able to dimerize and subsequently to form filaments. The involvement of phosphorylation of myosin II in this priming event is somewhat controversial. Although in higher eukaryotes the conformational change is dependent on phosphozylation, in Ancanthoamoeba, a lower eukaryote, the post-translational addition of phosphate is not required to effect the initial dimerization step. It is of note that the dimerization domains in myosin II of higher eukaryotes contain the sites for phosphorylation and it is probable that phosphorylation in this region is responsible for enabling myosin II to dimerize and subsequently form filaments. In Dictyostelium this situation is reversed in that the phosphorylation sites are outside the dimerization domain and phosphorylation at these sites is required to effect the disassembly of myosin filaments. In contrast to both these examples, Acanthoamoeba myosin II is phosphorylated in the dimerization domain but this modification is not necessary to enable myosin II monomers to dimerize in this species.

By far the most frequent example of enzymatic modification is the addition of phosphate to polypeptides by specific enzymes known as protein kinases. These enzymes have been identified as important regulators of the state of phosphorylation of target proteins and have been implicated as major players in regulating cellular physiology. For example, the cell-division-cycle of the eukaryotic cell is primarily regulated by the state of phosphorylation of specific proteins the functional state of which is determined by whether or not the protein is phosphorylated. This is determined by the relative activity of protein kinases which add phosphate and protein phosphatases which remove the phosphate moiety from these proteins. Clearly, dysfunction of either the kinases or phosphatases may lead to a diseased state. This is best exemplified by the uncontrolled cellular division shown by tumor cells. The regulatory pathway is composed of a large number of genes that interact in vivo to regulate the phosphorylation cascade that ultimately determines if a cell is to divide or arrest cell division.

Currently there are several approaches to analyzing the state of modification of target proteins in vivo:

1. In vivo labeling of cellular substrate pools with radioactive substrate or substrate precursor molecules to result in incorporation of labeled (for example, radiolabeled) moieties (e.g., phosphate, fatty acyl (including, but not limited to, myristoyl, palmityl, sentrin, methyl, actyl, hydroxyl, iodine, flavin, ubiquitin or ADP-ribosyls), which are added to target proteins. Analysis of modified proteins is typically performed by electrophoresis and autoradiography, with specificity enhanced by immunoprecipitation of proteins of interest prior to electrophoresis.
2. Back-labeling. The enzymatic incorporation of a labeled (including, but not limited to, with a radioactive and fluorescent label) moiety into a protein in vitro to estimate the state of modification in vivo.
3. Detection of alteration in electrophoretic mobility of modified protein compared with unmodified (e.g., glycosylated or ubiquitinated) protein.
4. Gel-shift analysis of radiolabeled oligonucleotides binding to modified proteins.
5. Thin-layer chromatography of radiolabeled fatty acids extracted from the protein of interest.
6. Partitioning of protein into detergent-rich or detergent layer by phase separation, and the effects of enzyme treatment of the protein of interest on the partitioning between aqueous and detergent-rich environments.
7. The use of cell-membrane-permeable protein-modifying enzyme inhibitors (e.g., Wortmannin, staurosporine) to block modification of target proteins and comparable inhibitors of the enzymes involved in other forms of protein modification (above).
8. Antibody recognition of the modified form of the protein (e.g., using an antibody directed at ubiquitin or carbohydrate epitopes), e.g., by Western blotting, of either 1- or 2-dimensional gels bearing test protein samples.
9. Lectin-protein interaction in Western blot format as an assay of the presence of particular carbohydrate groups (defined by the specificity of the lectin in use).
10. The exploitation of eukaryotic microbial systems to identify mutations in protein-modifying enzymes.

These strategies have certain limitations. Monitoring states of modification by pulse or steady-state labeling is merely a descriptive strategy to show which proteins are modified when samples are separated by gel electrophoresis and visualized by autoradiography. This is unsatisfactory, due to the inability to identify many of the proteins that are modified. A degree of specificity is afforded to this technique if it is combined with immunoprecipitation; however, this is of course limited by the availability of antibodies to target proteins. Moreover, only highly-expressed proteins are readily detectable using this technique, which may fail to identify many low-abundance proteins, which are potentially important regulators of cellular functions.

The use of enzyme inhibitors to block activity is also problematic. For example, very few kinase inhibitors have adequate specificity to allow for the unequivocal correlation of a given kinase with a specific kinase reaction. Indeed, many inhibitors have a broad inhibitory range. For example, staurosporine is a potent inhibitor of phospholipid/$Ca^{+2}$ dependant kinases. Wortmannin is some what more specific, being limited to the phosphatidylinositol-3 kinase family. This is clearly unsatisfactory because more than one biochemical pathway may be affected during treatment making the assignment of the effects almost impossible.

Finally, yeast (*Saccharomyces cervisiae* and *Schizosaccharomyces pombe*) has been exploited as a model organism for the identification of gene function using recessive mutations. It is through research, on the effects of these mutations that the functional specificities of many protein-modifying enzymes have been elucidated. However, these molecular genetic techniques are not easily transferable to higher eukaryotes, which are diploid and therefore not as genetically tractable as these lower eukaryotes.

Various epigenetic modifications of nucleic acids are also known, for example, methylation. Methylation of DNA is an epigenetic modification that can play an important role in the control of gene expression in mammalian cells (reviewed in Momparler & Bovenzi 2000, *J. Cell. Physiol.* 183(2):145–54 and Robertson & Jones, 2000, *Carcinogenesis* 21:461–467).

A non-limiting example of enzymatic modification of proteins is provided by the Ras proteins, which are a conserved group of polypeptides located at the plasma membrane which exist in either a GTP-bound active state or in a GDP-bound inactive state. This family of proteins operates in signal transduction pathways that regulate cell growth and differentiation. In higher eukaryotes, Ras is a key regulator that mediates signal transduction from cell surface tyrosine kinase receptors to the nucleus via activation of the MAP kinase cascade. Recent studies have demonstrated that Ras directly binds a serine/threonine kinase, Raf-1, a product of the c-raf-1 proto-oncogene, and that this association leads to stimulation of the activity of Raf-1 to phosphorylate MAP kinase kinase (MEK).

Another enzymatic modification is the addition of ubiquitin to selected polypeptides. This provides a key mechanism by which to control the abundance of important regulatory proteins, for example, GI and mitotic cyclins and the p53 tumor suppressor protein. Ubiquitin is a highly conserved 76-amino-acid cellular polypeptide. The role of ubiquitin in targeting proteins for degradation involves the specific ligation of ubiquitin to the $\epsilon$ group of lysine residues in proteins that are to be degraded or internalized from the plasma membrane. The ubiquitin tag determines the fate of the protein and results in its selective proteolysis. Recently a number of factors have been isolated and shown to be involved in the ubiquitination process.

The initial step in the addition of ubiquitin to a protein is the activation of ubiquitin by the ubiquitin activating enzyme, E1. This is an ATP-dependent step resulting in the formation of a thioester bond between the carboxyl terminal glycine of ubiquitin and the active site cysteine residue of E1. Activated ubiquitin then interacts with a second factor, the E2 protein. A thioester bond forms between the activated glycine residue of ubiquitin and a cysteine residue in a specific E2 protein. The E2 proteins represent a family of closely-related proteins encoded by different genes that confer specificity in the proteolytic process. The ligation of ubiquitin to target proteins is effected by the involvement of a further factor, a ubiquitin ligase, E3, of which a number are known (in yeast, reviewed by Hats & Siepmann, 1997, *FASEB J*. 11:1257–1268; in humans, see Honda et al, 1997, *FEBS Lett*. 420:25–27). E3 completes the final step of ubiquitination by attaching ubiquitin via the $\epsilon$ amino group on lysine residues in proteins to be targeted for degradation. Moreover, E3 is able to add ubiquitin to ubiquitin molecules already attached to target proteins, thereby resulting in polyubiquitinated proteins that are ultimately degraded by the multi-subunit proteasome.

International patent application number WO92/00388 describes an adenosine 3:5 cyclic monophosphate (cAMP) dependent protein kinase which is a four-subunit enzyme being composed of two catalytic polypeptides (C) and two regulatory polypeptides (R). In nature the polypeptides associate in a stoichiometry of $R_2C_2$. In the absence of cAMP the R and C subunits associate and the enzyme complex is inactive. In the presence of cAMP the R subunit functions as a ligand for cAMP resulting in dissociation of the complex and the release of active protein kinase. The invention described in WO92/00388 exploits this association by adding fluorochromes to the R and C subunits having different excitation/emission wavelengths. The emission from one such fluorophore following excitation effects a second excitation/emission event in the second fluorophore. By monitoring the fluorescence emission or absorption of each fluorophore, which reflects the presence or absence of fluorescence energy transfer between the two, it is possible to derive concentration of cAMP as a function of the association between the R and C subunits. Therefore, the natural affinity of the C subunit for the R subunit has been exploited to monitor the concentration of a specific metabolite, namely cAMP. The prior art teaches that intact, fluorophore-labeled proteins can function as reporter molecules for monitoring the formation of multi-subunit complexes from protein monomers.

Tsien et al. (WO97/28261) teach that fluorescent proteins having the proper emission and excitation spectra that are brought into physically close proximity with one another can exhibit fluorescence resonance energy transfer ("FRET"). The invention of WO97/28261 takes advantage of that discovery to provide tandem fluorescent protein constructs in which two fluorescent protein labels capable of exhibiting FRET are coupled through a linker to form a tandem construct. In the assays of the Tsien et al. application, protease activity is monitored using FRET to determine the distance between fluorophores controlled by a peptide linker and subsequent hydrolysis thereof. Other applications rely on a change in the intrinsic fluorescence of the protein as in the kinase assays of WO98/06737.

Our unpublished International Patent Application Number PCT/GB00/00674 discloses a method for monitoring activity of an enzyme. The method comprises performing a detection step to detect binding or dissociation of an isolated engineered binding domain and a binding partner therefor as a result of contacting one or both of said isolated engineered binding domain and said binding partner with said enzyme. The isolated engineered binding domain includes a site for enzymatic modification, and binds the binding partner in a manner dependent upon modification of the site. Detection of binding or dissociation of said isolated engineered binding domain and said binding partner as a result of said contacting is indicative of enzyme activity. In the method disclosed in PCT/GB00/00674, each of the binding domain and binding partner is required to be a polypeptide sequence.

There is a need in the art for efficient means of monitoring and/or modulating post-translational protein modification. Further, there is a need for developing a technique whereby the addition/removal of a modifying group can be monitored continuously during real time to provide a dynamic assay system that also has the ability to resolve spatial information. We have now found that, in addition to using polypeptide binding domains and binding partners as disclosed in PCT/GB00/00674, it is also possible to detect the activity of an enzyme by detecting the binding of a polypeptide to a nucleic acid sequence, such binding being modulated by enzymatic modification of the protein or the nucleic acid by the enzyme.

SUMMARY OF THE INVENTION

According to a first aspect of the present invention, we provide a method for monitoring the activity of an enzyme, the method comprising the steps of: (a) providing a binding domain which includes a site for enzymatic modification; (b) providing a binding partner which binds to the binding domain in a manner which is dependent upon modification of the site; (c) contacting the binding domain with the enzyme; and (d) detecting binding of the binding domain to the binding partner as an indication of the activity of the enzyme; in which one of the binding domain and binding partner comprises a polypeptide and the other of the binding domain and binding partner comprises a nucleic acid.

We provide, according to a second alternative aspect of the present invention, a method for monitoring the activity of an enzyme, the method comprising the steps of: (a) providing a binding domain which includes a site for enzymatic modification; (b) providing a binding partner which dissociates from the binding domain in a manner which is dependent upon modification of the site; (c) contacting the binding domain with the enzyme; and (d) detecting dissociation of the binding domain to the binding partner as an indication of the activity of the enzyme; in which one of the binding domain and binding partner comprises a polypeptide and the other of the binding domain and binding partner comprises a nucleic acid.

The binding domain may be an engineered binding domain, as defined below.

The binding domain may comprise a polypeptide, which may preferably comprise a sequence which directs modification by at least one of the following enzymes: a kinase, a phosphatase, a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD:Arginine ADP ribosyltransferase. The site may preferably comprise a sequence which directs modification by an enzyme selected from the group consisting of: protein kinase A (PKA), glycogen synthase kinase-3 (GSK-3), casein kinase II (CKII), Cdc2 kinase, cyclin E, cdk2, cyclin A, cdk2, cyclin B, cdc2, EnvZ, protein kinase-C (PKC) and heart muscle kinase (HMK).

In one embodiment, the binding domain comprises a CREB/ATF polypeptide or a fragment thereof and the binding partner comprises a CRE binding site or a fragment thereof. Alternatively, the binding domain may comprise a p53 polypeptide or a fragment thereof and the binding partner may comprise a p53 response element DNA or a fragment thereof. Other binding domain/binding partner pairs are also possible, for example, the binding domain may comprise an OmpR polypeptide or a fragment thereof and the binding partner an OmpF promoter or a fragment thereof; or the binding domain may comprise a HIV type-1 Rev polypeptide or a fragment thereof and the binding partner a. stem-loop IIB RNA.

Alternatively, the binding domain comprises a nucleic acid and further comprises a seqeunce which directs modification by a nucleic acid modifying enzyme. In one embodiment, the binding domain comprises a nucleic acid, in which case the binding domain preferably comprises a sequence which directs modification by a methylase or a demethylase. Preferably, the binding domain may comprise a sequence which directs DNA methylation or DNA demethylation. Preferably, the binding partner is a restriction enzyme, a transcription factor or a methyl binding protein.

The binding domain of the invention comprises a site for enzymatic modification. The site may permit addition or removal of a chemical moiety, and the addition or removal may each prevent or promote binding of the binding domain to the binding partner. In the case where the binding domain comprises a polypeptide, the chemical moeity that is added or removed is preferably selected from the group consisting of: a phosphate moiety, a ubiquitin moiety, a glycosyl moiety, an ADP-ribosyl moiety, a fatty acyl moiety and a sentrin moiety. Where the binding domain comprises a nucleic acid, the chemical moeity that is added or removed is preferably a methyl group.

Preferably, at least one of the binding domain and the binding partner comprises a detectable label. The detectable label preferably emits light; most preferably, the light is emitted as a result of fluorescence. The binding domain or the binding partner, or both, may further comprise a quencher for the detectable label. The detection step may comprise detection of a change in signal emission by the detectable label, and the method may further comprise exciting the detectable label and monitoring fluorescence emission. Other detectable labels useful according to the invention include radioactive labels, chemical labels or enzymatic labels, well known in the art.

As used herein, a "change in signal emission" refers to a difference in the signal emission of at least 10% or more (for example 10%, 20%, 50%, 100%, 500% etc. . . . ) relative the signal emission in a control sample in which a modulator of the invention is not present.

The method may further comprise the step of contacting the binding domain and the binding partner with an agent which modulates the activity of the enzyme. This step may be done prior to or after the detection step.

There is provided, according to a third alternative aspect of the invention, a method of screening for a candidate modulator of enzymatic activity of at least one of the following enzymes: a kinase, a phosphatase, a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD:Arginine ADP ribosyltransferase, the method comprising: (a) contacting a binding domain comprising a polypeptide, a binding partner therefor comprising a nucleic acid, and an enzyme with a candidate modulator of the enzyme, in which the binding domain includes a site for enzymatic modification and binds the binding partner in a manner that is dependent upon modification of the site by the enzyme, and in which at least one of the binding domain and the binding partner comprises a detectable label, and (b) monitoring the binding of the binding domain to the binding partner, in which binding or dissociation of the binding domain and the binding partner as a result of the contacting is indicative of modulation of enzyme activity by the candidate modulator of the enzyme.

We provide, according to a fourth alternative aspect of the invention, a method of screening for a candidate modulator of enzymatic activity of a methylase or a demethylase, the method comprising: (a) contacting a binding domain comprising a nucleic acid, a binding partner therefor comprising a polypeptide, and an enzyme with a candidate modulator of the enzyme, in which the binding domain includes a site for enzymatic modification and binds the binding partner in a manner that is dependent upon modification of the site by the enzyme, and in which at least one of the binding domain and the binding partner comprises a detectable label, and (b) monitoring the binding of the binding domain to the binding partner, in which binding or dissociation of the binding domain and the binding partner as a result of the contacting is indicative of modulation of enzyme activity by the candidate modulator of the enzyme.

Preferably, the detectable label emits light, more preferably, the light is emitted as a result of fluorescence. The monitoring may comprise measuring a change in energy transfer between a label present on the binding domain and a label present on the binding partner.

According to a fifth alternative aspect of the present invention, we provide a method of screening for a candidate modulator of enzymatic activity of at least one of the following enzymes: a kinase, a phosphatase, a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD:Arginine ADP ribosyltransferase, the method comprising: (a) contacting an assay system with a candidate modulator of enzymatic activity of the enzyme, and (b) monitoring binding of a binding domain comprising a polypeptide and a binding partner therefor comprising a nucleic acid in the assay system, in which the domain includes a site for enzymatic modification and binds the binding partner in a manner that is dependent upon modification of the site by at least one enzyme in the assay system, in which at least one of the binding domain and the binding partner comprises a detectable label, and in which binding or dissociation of the binding domain and the binding partner as a result of the contacting is indicative of modulation of enzyme activity by the candidate modulator of the enzyme.

As used herein, an "assay system" refers to any in vivo or in vitro system that supports and is preferably optimal for the methods of the invention. An "assay system" of the invention includes but is not limited to crude cellular extracts, cell free assay systems known in the art and described herein, cell lysates and whole cells.

There is provided, according to a sixth alternative aspect of the invention, a method of screening for a candidate modulator of enzymatic activity of a methylase or a demethylase, the method comprising: (a) contacting an assay system with a candidate modulator of enzymatic activity of the enzyme, and (b) monitoring binding of a binding domain comprising a nucleic acid and a binding partner therefor comprising a polypeptide in the assay system, in which the domain includes a site for enzymatic modification and binds the binding partner in a manner that is dependent upon modification of the site by at least one enzyme in the assay system, in which at least one of the binding domain and the binding partner comprises a detectable label, and in which binding or dissociation of the binding domain and the binding partner as a result of the contacting is indicative of modulation of enzyme activity by the candidate modulator of the enzyme.

The methods according to the various aspects of our invention may comprise real-time observation of association of a binding domain and its binding partner. The methods of our invention may involve binding domains and binding partners which bind to each other in 1:1 stoichiometry, in other words, a single molecule of a binding domain binds to a single molecule of a binding partner. Alternatively, multiple molecules (e.g., 2, 3, 4, 5 or more) of the binding domain may bind to a single molecule of a binding partner. Our methods therefore involve stoichiometries such as 2:1, 3:1, 4:1, 5:1, etc, depending on the nature of the binding domains and binding partners involved.

DETAILED DESCRIPTION OF THE INVENTION

The present invention encompasses the use of FRET or other detection procedures to monitor the association of a polypeptide and a nucleic acid. The polypeptides and/or nucleic acids may be labeled with fluorescent labels (protein or chemical), and FRET, fluorescence correlation spectroscopy, fluorescence anisotropy, monomer:excimer fluorescence or other techniques indicate the proximity of the polypeptide and the nucleic acid. The polypeptide and the nucleic acid comprise a binding domain/binding partner pair. Where the binding domain comprises a polypeptide, the binding partner comprises a nucleic acid, and vice versa. The polypeptide and the nucleic acid associate either in the presence or absence of a given enzymatic modification of a site in the binding domain. Therefore, the site for enzymatic modification is comprised in either the polypeptide or the nucleic acid of the binding domain/binding partner pair. The degree of binding of the two therefore reflects the modification state of the binding domain and, consequently, the level of activity of a relevant modifying enzyme.

Protein-nucleic acid interactions are a common feature of both eukaryotic and prokaryotic cells. The interaction may be between protein and DNA, usually for the control of transcription, or protein and RNA, usually for the control of translation. In either case, the interaction occurs between the protein and a specific sequence of DNA/RNA known as the binding site and may lead to activation or repression of transcriptional or translational function. A common feature of control of these protein-nucleic acid interactions is the degree of post-translational modification of the protein. Phosphorylation of the protein is the most common and most studied post-translational modification event responsible for regulation of the protein-nucleic acid interactions. Such modifications of the protein may either inhibit or enhance the protein-nucleic acid interactions.

The present invention is directed to a method of monitoring the activities of enzymes responsible for the post-translation modification of nucleic acid binding proteins by monitoring the extent of post-translational modification dependent protein-nucleic acid binding. Phosphorylation is the best-understood form of post-translational modification in regulating protein-nucleic acid interactions, but the methods of our invention may equally be applied to any other post-translational modification events, e.g., glycosylation, ribosylation, acetylation and geranylgeranylation, as well as any post-translation modification event known in the art.

The invention further provides methods which employ non-fluorescent labels including, but not limited to, radioactive labels and chemical labels. In addition, the invention encompasses methods which do not employ detectable labels; such methods include, but are not limited to, the detection of the inhibition or reconstitution of enzymatic activity, which inhibition or reconstitution results from modification-dependent binding or dissociation of a binding domain and a binding partner therefor.

The binding domain may comprise a polypeptide or a nucleic acid. As used herein, the term "binding domain" refers in a three-dimensional sense to the amino acid residues of a polypeptide or the nucleotide residues of a nucleic acid (as the case may be), required for modification-dependent binding between the polypeptide or nucleic acid and its binding partner. Where the binding domain comprises a polypeptide, its constituent amino acids may be either contiguous or non-contiguous. A polypeptide binding domain must include at least 1 amino acid, and may include 2 or more, preferably 4 or more (for example 5, 6, 7, 10, 20, 100 etc. . . . ), amino acids. Where the binding domain comprises a nucleic acid, the nucleotides of a nucleic acid binding domain may be either contiguous or non-contiguous, but must include at least 1 nucleotide residue, and may include 2 or more, preferably 4 or more (for example 5, 6, 7, 10, 20, 100 etc. . . . ), nucleotide residues. A polypeptide binding domain may include a full-length (i.e., the complete sequence) protein and a nucleic acid binding domain may include a full-length nucleic acid (i.e., the complete sequence of a gene or a gene transcript).

A polypeptide binding domain of use in the invention may be present on a polypeptide chain that consists solely of the binding domain amino acid sequence or may be present in the context of a larger polypeptide molecule (i.e., one which comprises amino acids other than those of the binding domain), which molecule may be either naturally-occurring or recombinant and, in the case of the latter, may comprise either natural or non-natural amino acid sequences. Where the binding domain comprises a nucleotide sequence, it may consist solely of the binding domain nucleic acid sequence or the binding domain may be present in the context of a longer nucleotide sequence (i.e., one which comprises nucleotides other than those of the binding domain). Such a molecule may be either naturally-occurring or recombinant and, in the case of the latter, may comprise either natural or non-natural nucleotide sequences. The invention also provides for polypeptides comprising modified amino acid residues, as well as nucleotide sequences comprising modified nucleic acid bases. The amino acids and nucleic acid bases can be modifed to include any modification known in the art.

As used herein, the term "engineered binding domain" refers to a binding domain, as defined above, which is an amino acid or nucleotide sequence that is altered (i.e., by insertion, deletion or substitution of at least one amino acid or nucleotide, as the case may be) such that the binding domain sequence is no longer as found in nature. The position of the altered amino acid or nucleotide is within the residues which form the domain. An "engineered binding domain" refers to a non-natural site that is not found in nature.

An engineered binding domain of use in the invention may be present on a polypeptide or nucleotide chain that consists solely of the engineered binding domain. sequence or may be present in the context of a larger polypeptide or nucleic acid molecule (i.e., one which comprises residues other than those of the engineered binding domain). This molecule may be either naturally-occurring or recombinant and, in the case of the latter, may comprise either natural or non-natural amino acids or nucleic acid sequences.

As used herein with regard to modification of the binding domain, the terms "site" and "site sufficient for the addition of" refer to an amino acid sequence or a nucleic acid sequence which is recognized by (i.e., a signal for) a modifying enzyme for the purpose of enzymatic modification (i.e., addition or removal of a "moiety" as defined below) of the polypeptide or nucleic acid or a portion thereof. A "site" additionally refers to the single amino acid or nucleotide residue which is modified. It is contemplated that a site comprises a small number of residues, as few as one but typically from 2 to 10, less often up to 30 amino acids, and further that a site comprises fewer than the total number of residues present in the polypeptide or nucleic acid. Such a site is present on the binding domain.

As used herein, the term "modification" or "enzymatic modification" refers to the addition or removal of a chemical "moiety", as described herein, to/from a site on a polypeptide or nucleotide chain and does not refer to other enzymatic events which do not involve addition or removal of such a moiety as described herein. This term therefore is not intended to include simple cleavage of the reporter molecule polypeptide backbone by hydrolysis of a peptide bond, but does include hydrolysis of an isopeptide bond (e.g., in the removal of ubiquitin).

As used interchangeably herein, the terms "moiety" or "chemical moiety" and "group" refer to one of the post-translationally added or removed groups referred to herein: i.e., including but not limited to one of a methyl, phosphate, ubiquitin, glycosyl, fatty acyl, sentrin or ADP-ribosyl moiety.

As used herein, the term "binding partner" refers to a polypeptide or nucleic acid, or fragment thereof, that binds to a binding domain, as defined herein, in a manner which is dependent upon the state of modification of a site for enzymatic modification present upon the binding domain. A "binding partner" refers in a three-dimensional sense to the amino acid residues of a polypeptide or the nucleotide residues of a nucleic acid (as the case may be), required for modification-dependent binding between the polypeptide or nucleic acid and its cognate binding domain. Where the binding partner comprises a polypeptide, its constituent amino acids may be either contiguous or non-contiguous. A polypeptide binding partner must include at least 1 amino acid, and may include 2 or more, preferably 4 or more (for example 5, 6, 7, 10, 20, 100 etc. . . . ), amino acids. Where the binding domain comprises a nucleic acid, the nucleotides of a nucleic acid binding partner may be either contiguous or non-contiguous, but must include at least 1 nucleotide residue, and may include 2 or more, preferably 4 or more (for example 5, 6, 7, 10, 20, 100 etc. . . . ), nucleotide residues. A polypeptide binding partner may include a full-length (i.e., the complete sequence of a protein) protein and a nucleic acid binding domain may include a full-length nucleic acid (i.e., the complete sequence of a gene or a gene transcript).

As used herein in reference to an engineered binding domain, the term "isolated" refers to a molecule or population of molecules that is substantially pure (i.e., free of contaminating molecules of unlike nature). "Isolated" refers to a population of molecules, the composition of which is less than 50%, preferably less than 40% and most preferably, 2% or less, contaminating molecules of an unlike nature.

As used herein, the terms "polypeptide" and "peptide" refer to a polymer in which the monomers are amino acids and are joined together through peptide or disulfide bonds. "Polypeptide" refers to either a full-length naturally-occurring amino acid chain or a "fragment thereof" or "peptide", such as a selected region of the polypeptide that is of interest in a binding assay and for which a binding partner is known or determinable, or to an amino acid polymer, or a fragment or peptide thereof, which is partially or wholly non-natural. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. "Peptide" refers to a short amino acid sequence that is 10–40 amino acids long, preferably 10–35 amino acids. Additionally, unnatural amino acids, for example, β-alanine, phenyl glycine and homoarginine may be included. Commonly-encountered amino acids which are not gene-encoded may also be used in the present invention. All of the amino acids used in the present invention may be either the D- or L-optical isomer. The L-isomers are preferred. In addition, other peptidomimetics are also useful, e.g., in linker sequences of polypeptides of the present invention (see Spatola, 1983, in *Chemistry and Biochemistry of Amino Acids Peptides and Proteins*, Weinstein, ed., Marcel Dekker, New York, p. 267). Modified amino acids or proteins are also useful for the methods of the present invention.

The term "synthetic", as used herein, is defined as that which is produced by in vitro chemical.

As used herein, the terms "protein", "subunit" and "domain" refer to a linear sequence of amino acids which exhibits biological function. This linear sequence, includes full-length amino acid sequences (e.g., those encoded by a full-length gene or polynucleotide), or a portion or fragment thereof, provided the biological function, as well as the post-translational-modification-dependent binding function, is maintained by that portion or fragment. The terms subunit and domain also may refer to polypeptides and peptides having biological function. A peptide useful in the invention will at least have a binding capability, i.e., with respect to binding as or to a binding partner, wherein the protein binding domain or binding partner binds to a binding partner or binding domain, respectively, with a Kd of about 10 $\mu$M or less. A peptide useful according to the invention may have another biological function that is a biological function of a protein or domain from which the peptide sequence is derived.

As used herein, the term "nucleic acid" includes both RNA and DNA, whether single or double stranded, constructed from natural nucleic acid bases or synthetic bases, or mixtures of these. "Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

As used herein in reference to the purity of a molecule or population thereof, the term "substantially" refers to that which is at least 50%, preferably 60–75%, more preferably from 80–95% and, most preferably, from 98–100% pure.

As used herein in reference to a polypeptide, the term "engineered" refers to an amino acid sequence that is altered with respect to a natural amino acid sequence and, in particular, is altered with respect to amino acids which contribute to modification-dependent binding of the polypeptide to a binding partner. As used with reference to a nucleic acid, this term refers to a nucleic acid sequence that is altered with respect to a natural nucleic acid sequence and in particular, is altered with respect to nucleic acid residues which contribute to modification-dependent binding of the nucleic acid to a binding partner. An "engineered" amino acid or nucleic acid sequence refers to a non-natural sequence that is not found in nature.

"Naturally-occurring" as used herein, as applied to a polypeptide or polynucleotide, refers to the fact that the polypeptide or polynucleotide can be found in nature. One such example is a polypeptide or polynucleotide sequence that is present in an organism (including a virus) that can be isolated from a source in nature. Where the polypeptide or polynucleotide is engineered as described herein so as to associate with a binding partner in a modification-dependent manner where it did not formerly do so or where it did so in a manner different, either in degree or kind, from that which it was engineered to do, it is no longer naturally-occurring but is "non-natural" and is derived from a naturally occurring polypeptide or polynucleotide.

In an assay of the invention, enzymatic modification is reversible, such that repeating cycles of addition and removal of a modifying moiety may be observed, although such cycles may not occur in a living cell found in nature.

As used herein, the term "associates" or "binds" refers to a polypeptide or nucleic acid as described herein and its binding partner having a binding constant sufficiently strong to allow detection of binding by fluorescent or other detection means, which are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a change in a signal compared to the bound state such that the signal is at least 5-fold, preferably 5–20-fold, and more preferably 20-fold or more greater (i.e., 30, 50, 100, 1000, 10,000-fold etc. . . . ) than the signal produced by the binding domain and the binding partner in the bound state, or where the signal produced is 5%, preferably 5–20%, more preferably 20–50% and most preferably 50–100% more or less than the signal produced by the binding domain and the binding partner in the bound state. The terms "substantially dissociated" and "dissociated" or "substantially unbound" or "unbound" include a total absence or loss of contact, such that the proteins are completely separated, as well as a partial absence or loss of contact, so that the body of the binding domain and binding partner are no longer in close proximity to each other but may still be tethered together or otherwise loosely attached, and thus have a dissociation constant greater than 10 $\mu$M (Kd). "Dissociated" or "unbound" also refers to a binding domain and a binding partner of the invention that have no contact regions. As used herein, a "contact region" refers to a region of a binding domain that physically contacts a binding partner and a region of a binding partner that physically contacts a binding domain. As used herein, a "change in a signal" refers to a signal that is at least 2-fold, preferably 2–20-fold, and more preferably 20-fold or more (for example 20,30, 40,50, 100, 100 or 10,000-fold etc. . . . ) than the signal produced by the binding domain and the binding partner in the bound state. A "change in a signal" also refers to a signal that is 5%, preferably 5–20%, more preferably 20–50% and most preferably 50–100% less than the signal produced by the binding domain and binding partner in the bound state. Thus, a "change in a signal" includes a complete loss of a signal. A "change in a signal" also refers to a signal that is at least 5%, preferably 5–20%, more preferably 20–50% and most preferably 50% or more (i.e., 50, 60, 75, 100, 500% etc. . . . ) greater than the signal produced by the binding domain and binding partner in the bound state. In many cases, the Kd will be in the mM range. The terms "complex" and, particularly, "dimer", "multimer" and "oligomer" as used herein, refer to the binding domain and its binding partner in the associated or bound state. More than one molecule of each of binding domain and its binding partner may be present in a complex, dimer, multimer or oligomer according to the methods of the invention.

As used herein, the term "binding sequence" refers to that portion of a polypeptide or nucleic acid comprising at least 1, but also 2 or more, preferably 4 or more, and up to 8, 10, 100 or 1000 contiguous (i.e., covalently linked) residues or even as many contiguous residues as are comprised by a full-length protein or nucleic acid, that are sufficient for modification-dependent binding to a binding partner. A binding sequence may exist on a polypeptide or nucleic acid molecule that consists solely of binding sequence residues or nucleotides or may, instead, be found in the context of a larger polypeptide or nucleic acid chain (i.e., one that comprises residues or nucleotides other than those of the binding sequence).

As used herein, the term "engineered binding sequence" refers to a binding sequence, as defined above, that is altered (e.g., by insertion, deletion or substitution of at least one amino acid or nucleotide residue) such that the fragment amino acid or nucleic acid sequence is no longer as found in nature and is "non-natural" according to the invention. As in the case of an "engineered binding domain", as defined above, the alteration must occur in those residues of a polypeptide or nucleotides of a nucleic acid which contribute to modification-state-dependent binding (that is, within the residues or nucleotides of the binding domain).

As used herein, the terms "binding polypeptide" and "binding nucleic acid" refer to molecules comprising one or more binding sequences, as defined above, which sequences are derived from a single, naturally-occurring polypeptide or nucleic acid molecule and are both necessary and, in combination, sufficient to permit modification-state-dependent binding of the binding polypeptide or binding of nucleic acid to its binding partner, wherein the sequences of the binding polypeptide or binding nucleic acid are either contiguous or non-contiguous. As used herein in reference to the component binding sequences of a binding polypeptide or binding nucleic acid, the term "non-contiguous" refers to binding sequences which are linked by intervening naturally-occurring, as defined herein, or non-natural amino acid or nucleotide sequences or other chemical or biological linker molecules such as are known in the art. The amino acids of a polypeptide that do not significantly contribute to the modification-state-dependent binding of that polypeptide to its binding partner may be those amino acids which are naturally present and link the binding sequences in a binding polypeptide or they may be derived from a different natural polypeptide or may be wholly non-natural. Likewise, the nucleotide residues of a nucleic acid sequence that do not significantly contribute to the modification-state-dependent binding of that nucleic acid to its binding partner may be those nucleotides which are naturally present and link the binding sequences in a binding nucleic acid or they may be derived from a different natural nucleic acid or may be wholly non-natural.

As used herein, the term "engineered binding polypeptide" refers to a binding polypeptide, as defined above, which polypeptide comprises at least one engineered binding sequence, as described above. If the binding sequences of an engineered binding polypeptide are linked by amino acid sequences (rather than chemical or other non-peptide linkers), a naturally-occurring amino acid sequence which links binding fragments in a binding polypeptide of use in an assay of the invention may be derived from the same natural polypeptide sequence from which one or more of the component binding fragments are drawn, including that from which an engineered binding fragment may have been derived, or may instead be derived from a different natural polypeptide.

The term "engineered binding nucleic acid" refers to a binding nucleic acid, as defined above, which nucleic acid comprises at least one engineered binding sequence, as described above. If the binding sequences of an engineered binding nucleic acid are linked by nucleotide sequences (rather than chemical or other non-nucleotide linkers), a naturally-occurring nucleic acid sequence which links binding fragments in a binding nucleic acid of use in an assay of the invention may be derived from the same natural nucleic acid sequence from which one or more of the component binding fragments are drawn, including that from which an engineered binding fragment may have been derived, or may instead be derived from a different natural nucleic acid.

As used herein the term "prevents binding" or "prevents association" refers to prevention of the association, as defined herein of a binding domain and a binding partner by the addition or removal of at least one chemical moiety (for example methyl, phosphate, ubiquitin, glycosyl, fatty acyl, sentrin or ADP-ribosyl group) to or from a binding domain. "Prevents binding or "prevents association" also refers to the prevention of the association, as defined herein, of a binding domain and a binding partner by the addition or removal of at least one chemical moiety (for example methyl, phosphate, ubiquitin, glycosyl, fatty acyl, sentrin or ADP-ribosyl group) to or from a binding domain thereof by at least 10%, preferably by 25–50%, highly preferably by 75–90% and, most preferably, by 95–100% relative to the association observed in the absence of such a modification under the same experimental conditions.

As used herein, the term "promotes binding" refers to increases the binding of the binding domain and its binding partner by at least two-fold, preferably 10- to 20-fold, highly preferably 50- to 100-fold, more preferably from 200- to 1000-fold, and, most preferably, from 200 to 10,000-fold.

It is preferred that at least one of the binding domain and the binding partner comprises a detectable label, more preferred that the detectable label emits light and most preferred that the light is emitted as a result of fluorescence. In certain embodiments of the invention, each of the binding domain and binding partner comprises a member of a pair of interactive signal generating moieties, for example a fluorescent moiety and a quencher or a donor and an acceptor.

A "fluorescent tag", "fluorescent label" or "fluorescent group" refers to either a fluorophore or a fluorescent protein or fluorescent fragment thereof. "Fluorescent protein" refers to any protein which fluoresces when excited with appropriate electromagnetic radiation. This includes proteins whose amino acid sequences are either natural or engineered. A "fluorescent protein" is a full-length fluorescent protein or fluorescent fragment thereof.

It is contemplated that with regard to fluorescent labels employed in FRET, the reporter labels are chosen such that the emission wavelength spectrum of one (the "donor") is within the excitation wavelength spectrum of the other (the "acceptor"). With regard to a fluorescent label and a quencher employed in a single-label detection procedure in an assay of the invention, it is additionally contemplated that the fluorophore and quencher are chosen such that the emission wavelength spectrum of the fluorophore is within the absorption spectrum of the quencher such that when the fluorophore and the quencher with which it is employed are brought into close proximity by binding of the binding domain upon which one is present with the binding partner comprising the other, detection of the fluorescent signal emitted by the fluorophore is reduced by at least 10%, preferably 20–50%, more preferably 70–90% and, most preferably, by 95–100%. A typical quencher reduces detection of a fluorescent signal by approximately 80%.

According to one preferred embodiment, one of the isolated binding domain and the binding partner comprises a quencher for the detectable label.

It is contemplated that at least a part of a substrate of an enzyme of use in the invention is transferred to a modification site on a binding domain of the invention. As used herein, the term "at least a part of a substrate" refers to a portion (e.g., a fragment of an amino acid or nucleic acid sequence, a moiety or a group, as defined above) which comprises less than the whole (for example, 99%, 90%, 80%, 50% etc. . . . of the substrate for the enzyme, the transfer of which portion to a modification site on a binding domain as defined above, is catalyzed by the enzyme.

An enzyme of use in the invention may be natural or recombinant or, alternatively, may be chemically synthesized. If either natural or recombinant, it may be substantially pure (i.e., present in a population of molecules in which it is at least 50% homogeneous), partially purified (i.e., represented by at least 1% of the molecules present in a fraction of a cellular lysate) or may be present in a crude biological sample. An enzyme that is useful according to the invention includes any enzyme that catalyzes a post translation modification reaction.

As used herein, the term "sample" refers to a collection of inorganic, organic or biochemical molecules which is either found in nature (e.g., in a biological- or other specimen) or in an artificially-constructed grouping, such as agents which might be found and/or mixed in a laboratory. Such a sample may be either heterogeneous or homogeneous.

As used herein, the interchangeable terms "biological specimen" and "biological sample" refer to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

In a method as described above, it is preferred that at least one of the binding domain and the binding partner is labeled with a detectable label, more preferred that the label emits light and most preferred that the light is emitted as a result of fluorescence. Preferably, the detection step is to detect a change in signal emission by the detectable label. According to one preferred embodiment, the method further comprises exciting the detectable label and monitoring fluorescence emission.

Preferably, the enzyme is one of the following enzymes: a methylase, a demethylase, a kinase, a phosphatase, a carbohydrate transferase (e.g., a UDP-N-Acetyl-glucosamine-Dolichyl-phosphate-N-acetylsglucosamine phosphotransferase or an O-G1cNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase.

It is preferred that the method further comprises the step, prior to or after the detection step, of contacting the binding domain and the binding partner with an agent which modulates the activity of the enzyme. As used herein with regard to a biological or chemical agent, the term "modulate" refers to enhancing or inhibiting the activity of a protein-modifying enzyme in an assay of the invention; such modulation may be direct (e.g., including, but not limited to, cleavage of- or competitive binding of another substance to the enzyme) or indirect (e.g., by blocking the initial production or, if required, activation of the modifying enzyme).

"Modulation" refers to the capacity to increase a measurable functional property of biological activity or process (e.g., enzyme activity or receptor binding) by at least 10%, 15%, 20%, 25%, 50%, 100% or more as compared to the level of activity or a process in the absence of a modulator; such an increase or decrease may be contingent on the occurrence of a specific event, such as activation of a signal transduction pathway, and/or may be manifest only in particular cell types. "Modulation" refers to the capacity to decease a measurable functional property of biological activity or process (e.g., enzyme activity or receptor binding) by at least 10%, 15%, 20%, 25%, 50% up to 100%, as compared to the level of activity or a process in the absence of a modulator; such an increase or decrease may be contingent on the occurrence of a specific event, such as activation of a signal transduction pathway, and/or may be manifest only in particular cell types.

"Modulation" also refers to the capacity to increase a measurable functional property or biological activity or process (e.g., enzyme activity or receptor binding) by at least 5-fold or more (i.e., 5, 6, 10, 20, 50, 100, 1000, 10,000-fold etc. . . . ) as compared to the level of activity or a process in the absence of a modulator.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 µM, 0.1 µM, 1.0 µM, and 10.0 µM, as described more fully hereinbelow. Test compound controls can include the measurement of a signal in the absence of the test compound or comparison to a compound known to modulate the target.

In a particularly preferred embodiment, the method of our invention comprises real-time observation of association of a binding domain and its binding partner.

As used herein in reference to monitoring, measurements or observations. in assays of the invention, the term "real-time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

Further features and advantages of the invention will become more fully apparent in the following description of the embodiments and from the claims.

The invention is based upon the discovery that a binding polypeptide or nucleic acid, or a polypeptide or nucleic acid comprising a binding domain or sequence, each as defined herein, which is capable of associating with a binding partner in a manner that is dependent upon the presence or absence of a "moiety", as described herein, at a site for enzymatic modification on the same polypeptide or nucleotide chain provides a sensitive system for assaying the activity of an enzyme that catalyzes modification at such a site and that measurements of enzymatic activity performed in such a system may be taken in real time.

A. Binding Polypeptides, Nucleic Acids Sequences and Domains of Use in the Invention An assay of the invention utilizes at least one polypeptide or nucleic acid chain which comprises a sequence that is capable of associating specifically with a second sequence, or "binding partner" as defined herein, in a modification-dependent manner. The ability of the polypeptide or nucleic acid chain to associate with the binding partner may be intrinsic to the molecule, or may be added by engineering.

i. Post-translational Protein Modifications

ADP-ribosylation

Mono-ADP-ribosylation is a post-translational modification of proteins which is currently thought to play a fundamental role in cellular signaling. A number of mono-ADP-ribosyl-transferases have been identified, including endogenous enzymes from both bacterial and eukaryotic sources and bacterial toxins. A mono-ADP-ribosylating enzyme, using as substrates the protein to be modified and nicotinamide adenine dinucleotide (NAD$^+$), is NAD:Arginine ADP ribosyltransferase (Zolkiewska et al., 1992, *Proc. Natl. Acad. Sci. U.S.A.* 89:11352–11356). The reactions catalyzed by bacterial toxins such as cholera and pertussis toxin are well understood; the activities of these toxins result in the permanent modification of heterotrimeric G proteins. Endogenous transferases are also thought to modify G proteins and therefore to play a role in signal transduction in the cell (de Murcia et al., 1995, *Trends Cell Biol.* 5:78–81). The extent of the effects that ADP-ribosylation can mediate in the cell is illustrated by the example of brefeldin A, a fungal toxin metabolite of palmitic acid. This toxin induces the mono-ADP-ribosylation of BARS-50 (a G protein involved in membrane transport) and glyceraldehyde-3-phosphate dehydrogenase. The cellular effects of brefeldin A include the blocking of constitutive protein secretion and the extensive disruption of the Golgi apparatus. Inhibitors of the brefeldin A mono-ADP-ribosyl-transferase reaction have been shown to antagonize the disassembly of the Golgi apparatus induced by the toxin (Weigert et al., 1997, *J. Biol. Chem.* 272:14200–14207). A number of amino acid residues within proteins have been shown to function as ADP-ribose acceptors. Bacterial transferases have been identified which modify arginine, asparagine, cysteine and diphthamide residues in target proteins. Endogenous eukaryotic transferases are known which also modify these amino acids, in addition there is evidence that serine, threonine, tyrosine, hydroxyproline and histidine residues may act as ADP-ribose acceptors but the relevant transferases have not yet been identified (Cervantes-Laurean et al., 1997, *Methods Enzymol.* 280:275–287 and references therein).

Poly-ADP-ribosylation is thought to play an important role in events such as DNA repair, replication, recombination and packaging and also in chromosome decondensation. The enzyme responsible for the poly-ADP-ribosylation of proteins involved in these processes is poly (ADP-ribose) polymerase (PARP; for *Drosophila melanogaster* PARP, see GenBank Accession Nos. D13806, D13807 and D13808). The discovery of a leucine zipper in the self-poly(ADP-ribosyl)ation domain of the mammalian PARP (Uchida et al., 1993, *Proc. Natl. Acad. Sci. U.S.A.* 90:3481–3485) suggested that this region may be important for the dimerization of PARP and also its interaction with other proteins (Mendoza-Alvarez et al., 1993, *J. Biol. Chem.* 268:22575–22580).

Specific examples of ADP ADP-ribosylation sites are those found at $Cys_3$ and $Cys_4$ (underlined) of the B-50 protein (Coggins et al., 1993, *J. Neurochem.* 60:368–371; SwissProt Accession No. P06836):

ML<u>CC</u>MRRTKQVEKNDDD and Pγ (the γ subunit of cyclic CMP phophodiesterase; Bondarenko et al., 1997, *J. Biol. Chem.* 272:15856–15864; GenBank Accession No. X04270):

FK<u>QRQTRQ</u>FK.

Ubiquitination

Ubiquitination of a protein targets the protein for destruction by the proteosome. This process of destruction is very rapid ($t_{1/2}$~60 seconds), and many proteins with rapid turnover kinetics are destroyed via this route. These include cyclins, p53, transcription factors and transcription regulatory factors, among others. Thus, ubiquitination is important in processes such as cell cycle control, cell growth, inflammation, signal transduction; in addition, failure to ubiquitinate proteins in an appropriate manner is implicated in malignant transformation. Ubiquitin is a 76-amino-acid protein which is covalently attached to a target protein by an isopeptide bond, between the ε-amino group of a lysine residue and the C-terminal glycine residue of ubiquitin. Such modification is known as mono-ubiquitination, and this can occur on multiple Lys residues within a target protein. Once attached, the ubiquitin can itself be ubiquitinated, thus forming extended branched chains of polyubiquitin. It is this latter state which signals destruction of the target protein by the proteosome. In the process of destruction, it appears that the polyubiquitinated protein is taken to the proteosome via a molecular chaperone protein, the ubiquitin molecules are removed undamaged (and recycled) and the target is degraded.

Ubiquitination is a complex process, which requires the action of three enzymes: Ubiquitin activating enzyme E1 (for human, GenBank Accession No. X56976), ubiquitin conjugating enzyme E2, also referred to as the ubiquitin carrier protein (for human, 17 kDa form, GenBank Accession No. X78140), and ubiquitin protein ligase E3α (UBR1; human, GenBank Accession No. AF061556). There are multiple forms of each of these enzymes in the cell, and the above examples are, therefore, non-limiting.

The signals contained within a protein which determine whether the protein is subject to the process of ubiquitination and destruction are two-fold: first, the identity of the N-terminal amino acid (so called N-end rule, Varshavsky, 1996, Proc. Natl. Acad, Sci. U.S.A. 93:12142–12149), and secondly the presence of a suitably positioned Lys residue in the protein (Varsbavsky, 1996, supra). This Lys can be up to ~30 amino acids away from the N-terminus in experimental examples studied where the N-terminus is a flexible, poorly-structured element of the protein (Varshavsky, 1996, supra) or could potentially be anywhere in the sequence where this presents it at an appropriate location relative to the N-terminus. An appropriate location is one which allows interaction of both the N-terminal residue and this integral lysine with the enzyme(s) responsible for ubiquitination, presumably simultaneously. The Lys residue becomes ubiquitinated, and the process of destruction is initiated. N-terminal residues can be classed as stabilizing (s) or destabilizing (d), and the inclusion of an amino acid in one of these broad classes is species-dependent (prokaryotes differ from yeast, which differs from mammals (Varshavsky, 1996, supra).

In a dimeric (or other oligomeric protein) the destabilizing N-terminal residue and the internal Lys can be in cis (on a single peptide), but may also be in trans (on two different polypeptides). The trans-recognition event will only take place while the complex is physically associated. Only the ubiquitinated subunit is proteolyzed (Varshavsky, 1996, supra).

Two examples of ubiquitination sites from natural proteins, IκB (Dai et al., 1998, J. Biol. Chem. 273:3562–3573; GenBank Accession No. M69043) and β-galactosidase (Johnson et al., 1990, Nature 346:287–291) are as follows:

IκB NH$_3$-MFQAAERPQEWAMEGPRDGL KKERLLDDRH-COOH

β-galactosidase NH$_3$-HGSGAWLLPVSLVKRKTTLAP-COOH where the ubiquitinated lysine residue is underlined for each (e.g., Lys$_{15}$ and Lys$_{17}$ for β-galactosidase).

According to the invention, a ubiquitination assay measures the addition of ubiquitin to-, rather than the destruction of-, a polypeptide binding domain.

Glycosylation

N-linked glycosylation is a post-translational modification of proteins which occurs in the endoplasmic reticulum and Golgi apparatus and is utilized with some proteins en route for secretion or destined for expression on the cell surface or in another organelle. The carbohydrate moiety is attached to Asn residues in the non-cytoplasmic domains of the target proteins, and the consensus sequence (Shakineshleman, 1996, Trends Glycosci Glycotech. 8:115–130) for a glycosylation site is NxS/T, where x cannot be proline or aspartic acid. N-linked sugars have a common five-residue core consisting of two GlcNAc residues and three mannose residues due to the biosynthetic pathway. This core is modified by a variety of Golgi enzymes to give three general classes of carbohydrate known as oligomannosyl, hybrid and lactosamine-containing or complex structures (Zubay, 1998, Biochemistry Wm. C. Brown Publishers). An enzyme known to mediate N-glycosylation at the initial step of synthesis of dolichyl-P-P-oligosaccharides is UDP-N-Acetylglucosamine-Dolichyl-phosphate-N-acetylsglucosamine phosphotransferase (for mouse, GenBank Accession Nos. X65603 and S41875).

Oxygen-linked glycosylation also occurs in nature with the attachment of various sugar moieties to Ser or Thr residues (Hansen et al., 1995, Biochem. J. 308:801–813). Intracellular proteins are among the targets for O-glycosylation through the dynamic attachment and removal of O-N-Acetyl-D-glucosamine (O-G1cNAc; reviewed by Hart, 1997, Ann. Rev. Biochem. 66:315–335). Proteins known to be O-glycosylated include cytoskeletal proteins, transcription factors, the nuclear pore protein complex, and tumor-suppressor proteins (Hart, 1997, supra). Frequently these proteins are also phosphoproteins, and there is a suggestion that O-G1cNAc and phosphorylation of a protein play reciprocal roles. Furthermore, it has been proposed that the glycosylation of an individual protein regulates protein:protein interactions in which it is involved.

Specific sites for the addition of O-G1cNAc are found, for example, at Ser$_{277}$, Ser$_{316}$ and Ser$_{383}$ of p67$^{SRF}$ (Reason et al., 1992, J. Biol. Chem. 267:16911–16921; GenBank Accession No. J03161). The recognition sequences encompassing these residues are shown below:

$^{274}$GTTSTIQTAP $^{313}$SAVSSADGTVLK $^{374}$DSSTDLTQTSSSGTVTLP

The identity of sites of O-G1cNAc is additionally known for a small number of proteins including c-myc (Thr$_{58}$, also a phosphorylation site; Chou et al., 1995, J. Biol. Chem. 270:18961–18965), the nucleopore protein p62 (see Reason et al., 1992, supra):

MAGGPADTSDPL and band 4.1 of the erythrocyte (see Reason et al., 1992, supra):

AQTITSETPSSTT

The site at which modification occurs is, in each case, underlined. The reaction is mediated by O-G1cNAc transferase (Kreppel et al., 1997, J. Biol. Chem. 272:9308–9315). These sequences are rich in helix breaking residues (e.g., G and P) and may be difficult to incorporate into a helical framework.

Prenylation (Fatty Acylation)

The post-translational modification of proteins with fatty acids includes the attachment of myristic acid to the primary amino group of an N-terminal glycine residue (Johnson et al., 1994, Ann. Rev. Biochem. 63:869–914) and the attachment of palmitic acid to cysteine residues (Milligan et al., 1995, Trends Biochem. Sci. 20:181–186).

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (Ras and MAP kinase, Itoh et al., 1993, J. Biol. Chem. 268:3025-); Ras and adenylate cyclase (in yeast; Horiuchi et al., 1992, Mol. Cell. Biol. 12:4515-) or with regulatory proteins (Shirataki et al., 1991, J. Biol. Chem. 266:20672–20677). The prenylation status of Ras is important for its oncogenic properties (Cox, 1995, Methods Enzymol. 250:105–121) thus interference with the prenylation status of Ras is considered a valuable anti-cancer strategy (Hancock, 1993, Curr. Biol. 3:770).

Sentrinization

Sentrin is a novel 101-amino acid protein which has 18% identity and 48% similarity with human ubiquitin (Okura et al., 1996, *J. Immunol.* 157:4277–4281). This protein is known by a number of other names including SUMO-1, UBL1, PIC1, GMP1 and SMT3C and is one of a number of ubiquitin-like proteins that have recently been identified. Sentrin is expressed in all tissues (as shown by Northern blot analysis), but mRNA levels are higher in the heart, skeletal muscle, testis, ovary and thymus.

The sentrinization of proteins is thought to involve the ubiquitin-conjugating enzyme Ubc9 (Gong et al., 1997, *J. Biol. Chem.* 272:28198–28201). The interaction between these two proteins in the yeast two-hybrid screen is very specific, suggesting that this is a biologically relevant phenomenon. The interaction is dependent upon the presence of the conserved C-terminal Gly-Gly residues present in sentrin (Gong et al., 1997, supra). The conjugation of sentrin to other proteins via $Gly_{97}$ requires the cleavage of the C-terminal four amino acids of the protein, His-Ser-Thr-Val.

One important protein shown to be modified by the addition of sentrin is the Ran-specific GTPase-activating protein, RanGAP1, which is involved in nuclear import of proteins bearing nuclear-localization signals (Johnson & Hochstrasser, 1997, *Trends Cell Biol.* 7:408–413). Conjugation of RanGAP1 and sentrin is essential both for the targeting of RanGAP1 to its binding partner on the nuclear pore complex (NPC) and for the nuclear import of proteins. Sentrin itself does not bind with high affinity to the NPC and it is, therefore, likely that it either provokes a conformational change in RanGAP1 that exposes a binding site or, alternatively, that the binding site is formed using both sentrin and RanGA.P1 sequences. There is evidence to suggest that the conjugation of sentrin to RanGAP1 is necessary for the formation of other sentrinized proteins (Kamitani et al., 1997, *J. Biol. Chem.* 272:14001–14004) and that the majority of these sentrinized proteins are found in the nucleus.

Sentrin has been shown in yeast two-hybrid screens to interact with a number of other proteins, including the death domains of Fas/APO1 and the TNF receptors, PML, RAD51 and RAD52 (Johnson & Hochstrasser, 1997, supra). These interactions implicate sentrin in a number of important processes. Fas/APO1 and TNF receptors are involved in transducing the apoptosis signal via their death domains. Ligation of Fas on the cell surface results in the formation of a complex via death domains and death-effector domains, triggering the induction of apoptosis. The overexpression of sentrin protects cells from both anti-Fas/APO and TNF-induced cell death (Okura et al., 1996, supra). It is not clear whether this protection is achieved simply by preventing the binding of other proteins to these death domains or whether a more complex process is involved, possibly one involving the ubiquitin pathway.

The interaction of sentrin with PML (a RING finger protein) is important, as it points to a disease state in which this protein may play a role. In normal myeloid cells, PML is found in a nuclear multiprotein complex known as a nuclear body. These nuclear bodies are disrupted in acute promyelocytic leukemia, where a chromosomal translocation generates a fusion between regions of the retinoic acid receptor cc and PML. This disruption can be reversed by treatment with retinoic acid. It has been shown that PML is covalently modified at multiple sites by members of the sentrin family of proteins (but not by ubiquitin or NEDD8). Two forms of the aberrant fusion protein have been identified, neither of which is modified by sentrin. It is, therefore, thought that differential sentrinization of the normal and aberrant forms of PML may be important in the processes underlying acute promyelocytic leukemia and may help in the understanding of the biological role of the PML protein (Kamitani et al., 1998, *J. Biol. Chem.* 273:3117–3120).

Phosphorylation Kinase and Phosphatases

A particularly important post-translational modification for which a large number of enzymes and targets have been identified is phoshorylation and dephosphorylation. The art is replete with references to protein kinases and phosphatases and their targets, including consensus phosphorylation motifs (such as -SQ- or -TQ- for the DNA dependent protein kinase (DNA-PK).

Some non-limiting examples of kinases and their sites for post-translational modification are presented in Table 1 below (phosphorylation/dephosphorylation).

Further examples of protein kinases identified to date include the protein tyrosine kinase subfamily (such as PDGF receptors, EGF receptors, src family kinases (see Brown & Cooper, 1996, *Biochimica and Biophysica Acta* 1287:121–149 for a review), the JAK kinase family (such as JAK1, JAK2 and tyk2), Erb B2, Bcr-Abl, Alk, Trk, Res/Sky for a detailed review see Al-Obeidi et al., 1998, *Biopolymers (Peptide Science)* Vol. 47:97–223), the MAP kinase pathway subfamily (such as the MAP family, the ERK family, the MEK family, the MEKK family, RAF-1 and JNK), the cyclin-dependent kinase subfamily (such as $p_{34}cdc2$ and cdk2—see Nigg, 1995, *Bioessays* 17:471–480 for a review), Wee1/Myt1, polo-like kinases (such as p1k1, P1x1, POLO, Snk, Fnk/Prk Sak-a, Sak-b—see Lane & Nigg, 1997, *Trends in Cell Biol.* 7:63–68), the receptor serine kinase subfamily, protein kinase C (PK-C), cyclic-AMP dependent kinase (PK-A), cyclic-GMP dependent kinase, $Ca^{2+}$/calmodulin dependent kinases (such as CaM kinase I, II and IV), DNA dependent protein kinase, phosphoinositide 3-kinases, PDK-1, the p21-activated protein kinase family (PAKs), such as Pak1, Pak2 and Pak3—see Sells & Chernoff, 1997, *Trends in Cell Biol.* 7:162–167), p70 S6 kinase, IκB kinase, casein kinase II, glycogen-synthase kinases.

A discussion of particular kinase pathways involved in signal transduction is given in chapter 35 of Lewin, 1997, *Gene VI*, Oxford University Press. Details of recognition and binding domains for a variety of kinases are given in Kuriyan & Cowburn, 1997, *Annu. Rev. Biophys. Biomol. Struc.* 26:259–288.

Some specific examples of kinases whose activity may be studied using the methods of the invention include the src family tyrosine kinases Lck and Fyn, that phosphorylate the TCR ζ chain, and are known to be involved in signal transduction associated with T cell receptor stimulation. The TCR ζ chain comprises specific tyrosine residues present in immunoreceptor tyrosine-based activation motifs (ITAMs) that are phosphoiylated by Lck and Fyn (Kuriyan & Cowbum, 1997, ibid.).The SH2 domain of another tyrosine kinase, ZAP70 binds to phosphorylated TCR ζ. Thus TCR ζ ITAM and ZAP70 SH2 represent binding domains and binding partners that may be of interest in studying the activity of the kinases Lck and Fyn (see Elder et al., 1994, *Science* 264:1596–1599 and Chan et al., 1994, *Science*, 264:1599–1601).

Another example is the IgE receptor γ subunit and the SH2 domain of Syk that may be used to study the activity of the Lyn kinase.

Examples of phosphatase identified to date fall into three main families (for review see Barford et al., 1998, *Annu. Rev. Biophys. Biomol. Struc.* 27:133–164). The PPP family includes the following catalytic subunits: PP1c, PP2Ac, PP2B, PPP1, PPP2A and PPP5 and the following regulatory subunits: NIPP-1, RIPP-1, p53BP2, ,134.5, PR65, PR55, PR72, PTPA, SV40 small T antigen, PPY, PP4, PP6 and PP5.

The PPM family includes pyruvate dehydrogenase phosphatase and Arabidopsis ABI1.

The protein tyrosine phosphatase family includes PTP1B, SHP-1, SHP-2 (cytosolic non-receptor forms), CD45 (see Thomas & Brown, 1999, *Trends in Immunol.* 20:406 and Ashwell & D'Oro, 1999, *Trends in Immunol.* 20:412 for further details), RPTP (receptor-like, transmembrane forms) and cdc25, kinase-associated phosphatase and MAP kinase phosphatase-1 (dual-specificity phosphatases). PTP1B is known to associate with the insulin receptor in vivo (Bandyopadhyay et al., 1997, *J. Biol. Chem.* 272:1639–1645).

TABLE 1

| Kinase | Consensus Sequence | GenBank No./Reference |
|---|---|---|
| CAMP-dependent protein kinase | -RRXRRXS/T- | Cα subunit M34181<br>RJIβ subunit M31158 |
| Myosin Heavy Chain kinase | -KXXSX- | Trends in Biochem. Sci. (1990) 15:342–346. |
| Myosin Heavy Chain kinase | -RXT- | M93393 |
| Calmodulin-Dependent protein kinase II | -RXXSX- | A chain J02942<br>β chain M16112<br>δ chain J05072<br>γ chain J04063 |
| cGMP-dependent protein kinase | -XSRX- | β isozyme Y07512 |
| Protein kinase C | -XRXXSXRX- | Trends in Biochem. Sci. (1990) 15:342–346. |
| S6 kinase II | -XRXXSX- | α2 isozyme L07599, L07601 |
| dsRNS kinase pp68 | -SELSRR- | Trends in Biochem. Sci. (1990) 15:342–346. |
| Casein kinase I | -XSXXSX- | α isoform X80693 |
| Mammary gland casein kinase | -XSXEX- | Trends in Biochem. Sci. (1990) 15:342–346. |
| Glycogen synthase kinase 3 | -XSXXXSX- | α isoform L40027 |

X signifies any amino acid.
Consensus sequences are taken from Trends Biochem. Sci. (1990) 15:342–346.
Further examples are tabulated in Pearson & Kemp, 1991, Methods Enzymol. 200:62–81.

ii. Assay of Enzymatic Activity According to the Invention

A large number of assays can be conceived, based upon the principles outlined above. The principle can be summarized, in this case for phosphorylation, as follows:

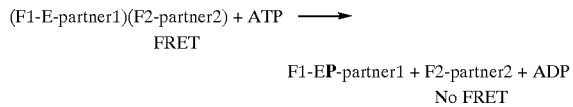

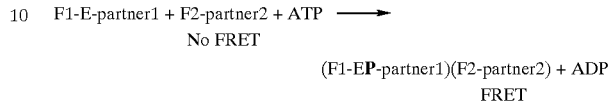

The following alternative assay format also is envisaged:

where

E=phosphorylation site

P=phosphorylation

F1=donor fluorophore

F2=acceptor fluorophore

FRET=Fluorescent resonance energy transfer

Table 2 below shows examples of phosphorylation dependent binding of proteins to specific nucleic acid sequences (binding sites). Any of the proteins shown in Table 2, or a fragment capable of binding a cognate nucleic acid sequence, may be used in conjunction with a nucleic acid sequence comprising the binding site, in the methods of our invention. For example, the CREB protein may be used as a binding domain together with the CRE binding site as a binding partner, in order to assay the activity of protein kinase A by measuring the increase of binding induced by phosphorylation of CREB. The same pair may be used to assay the activity of GSK-3 by measuring the dissociation caused by phosphorylation of CREB by GSK-3. Association and/or dissociation may be detected using a FRET assay as described above.

TABLE 2

| Protein | Function/System | Kinase | Phosphorylation effect | Comments |
|---|---|---|---|---|
| CREB/ATF[1] | Cyclic AMP response elements (CRE) | PKA<br>GSK-3 | Increases binding<br>Releases bound CREB | Required for cellular growth and development<br>Member of bZIP family |
| SRY (TCF-1 LEF-1 SOX)[2] | Sex determining gene | PKA | Increases binding to DNA | SKY belongs to a subclass of HMG box containing proteins that bind to DNA |
| TAL1[3] | Involved in T-cell acute lymphoblastic leukemia | PKA | Increases binding to DNA | TAL1 belongs to a HLH family of transcription factors<br>Needs E12 protein for DNA binding |
| HNF4[4] | Hepatocyte nuclear factor 4 | PKA | Decreases binding to DNA | Also PKB? |
| NGF1-B[5] | | PKA | Decreases binding to DNA | |
| WT1[6]<br>Zinc finger family<br>4 different isoforms | Tumor suppressor gene<br>Mutations cause kidney tumors<br>Wilms tumor occurs in 1 in 10,000 children | PKA | Decreases binding to DNA | Transcriptional activator or repressor depending on promoter<br>Binds and suppresses<br>P releases suppression |
| NRF-1[7] | Nuclear respiratory factor | CKII | Increases binding to DNA | P causes an intrinsic change in NRF-1 dimer, enhancing DNA binding |
| MEF2C[8]<br>Member of | Myocyte enhancer factor | CKII | Increases binding to DNA | Possible association with Muscular Dystrophy |

TABLE 2-continued

| Protein | Function/System | Kinase | Phosphorylation effect | Comments |
|---|---|---|---|---|
| MADS box transcription factor family. | Required for differentiation of skeletal, cardiac and visceral muscle cells | | | |
| Topoisomerase II[9] | Essential for cell proliferation | CKII | Increases binding to DNA | |
| hOR[10] | Human Estrogen receptor | CKII | Increases binding to DNA | |
| HMG-1[11] | Mammalian high mobility group nonhistone protein | Cdc2 Kinase | Decreases binding to DNA | Also phosphorylated by CMI and PKC |
| E2F-1[13] | DNA replication and cell cycle regulation Binds to adenovirus E2 promoter | CyclinA/ Cdk2 | Decreases binding to DNA | E2F also binds to PRB and DP1 in a P-dependent manner A simple E2F-1/DNA binding event has been demonstrated |
| P53[14] | Cell regulation | CyclinA/ Cdk2/ CyclinB | Increases binding to DNA | p53 binds to a diverse set of DNA sequences including WAF 1, p21, cip 1 sites Phosphorylation by these kinases confers binding specificity |
| OmpR[15] | Controls the expression of ompF and ompC in E. coli | Histidine kinase, EnvZ | Increases binding to DNA | Natural E. coli protein and Kinase |
| Ferritin[16] | Regulatory role in PCK mRNA degradation | PKA | Decreases binding to RNA | |
| SRp40[17] | Regulation of alternative splicing | Not known. | Increases binding to RNA | A member of SR protein family of splicing factors. Phosphorylation was achieved by incubation with HeLa S100 |
| HIV type-1 Rev protein[18] | Post transcriptional regulator of virion gene expression | PKC or HMK | Increases binding to RNA | P-H6Rev binds to stem-loop IIB RNA ligand 7-fold more tightly than H6Rev. |

Table 2.
Examples of phosphorylation dependent binding of proteins to specific Nucleic acid sequences. (Binding sites). References:
[1]Bullock & Hebener, 1998, Biochemistry 37:3795–3809;
[2]Desclozeaux et al., 1998, J. Biol. Chem. 273:7988–7995;
[3]Prasad & Brandt 1997, J. Biol. Chem. 272:11457–11462;
[4]Viollet et al., 1997, Mol. Cell Biol. 17:4208–19;
[5]Hirata et al., 1993, 1. Biol. Chem. 268:24808–12;
[6]Sakamoto et al., 1997, Oncogene 15:2001–2012;
[7]Gugneja & Scarpulla, 1997, J. Biol Chem. 272:18732–9;
[8]Molkentin et. al, 1996, J. Biol. Chem. 271:17199–17204;
[9]Dang et al., 1994, J. Mol. Biol. 243:10–24;
[10]Castano et al., 1997, Biochem. J. 326:149–157;
[11]Wisniewski et al., 1999, J. Biol. Chem. 274:20116–22;
[12]Hara et al, 1997, EMBO J. 16:332–42;
[13]Peeper et al., 1995, Oncogene 10:39–48;
[14]Wang & Prives, 1995, Nature 376:88–91;
[15]Head et al., 1998, J. Mol. Biol. 281:857–870;
[16]Heise et al., 1997, J. Biol. Chem. 272:20222–20229;
[17]Tacke et al., 1997, PNAS (USA) 94:1148 1153;
[18]Fouts et al., 1997, Biochemistry 36:13256–13262.

The methods of our invention may also be used to assay other enzyme activities besides phosphorylation, for example, any of the activities shown in Tables 3 and below, as well as any modifying enzyme activity. This may be done by modifying a polypeptide binding domain which naturally binds to a nucleic acid partner sequence. Such a polypeptide is engineered to include an engineered binding domain containing a modification site for the relevant enzyme by methods known in the art, in such a way that its ability to bind its nucleic acid partner becomes dependent on its modification state by the enzyme in question. For example, a DNA binding protein may be modified to include a ubiquitination site, so that it is unable to bind its cognate DNA sequence when ubiquitinated, but is able to do so when it is not ubiquitinated.

TABLE 3

| Modification | Protein Source | Consensus Sequence/Sequence | Reference/ GenBank No. |
|---|---|---|---|
| | | Modified residues indicated in bold Residues forming part of the recognition site are shown in italics | |
| ADP-Ribosylation | B-50 | [1]MLCCMRRTKQVEK ND DD | Coggins et al. 1993, J.Neurochem. 60:368–71 |
| | γ subunit of cGMP phosphodiesterase | [30]FKQRQTRQFK | X04270 |

TABLE 3-continued

| Modification | Protein Source | Consensus Sequence/Sequence | Reference/GenBank No. |
|---|---|---|---|
| Ubiquitination | IκB | ¹MFQAAERPQEWAM EG PRDGLKKERLLDDR H | M69043 |
|  | B-Galactosidase | ¹HGSGAWLLPVSLVK RKTTLAP | Johnson et al., 1990, Nature 346:287–291 |
| N-Myristoylation | Src | ¹GSSKSKPKD | Resh, 1994, Cell 76:411–413 |
|  | Lyn | ¹GCIKSKRKD | Resh, 1994, supra |
|  | Yes | ¹GCJKSKEDK | Resh, 1994, supra |
|  | Fyn | ¹GCVQCKDKE | Resh, 1994, supra |
|  | Gα | ¹GC17LSAEDK | Resh, 1994, supra |
| Palmitylation | Lyn | ¹GCIKSKRKD | M64608 |
|  | Fyn | ¹GCVQCRDKE | M14676 |
|  | Gαi2 | ¹GCTLSAEDK | Milligan et al., 1995, Trends Biochem. Sci. 20:181–186 |
| N-Glycosylation |  | -NXS/T- X can be any amino acid except P | Shakineshleman, 1996, Trends in Glycoscience and Glycotechnology 8:115–130 |
| O-Glycosylation | p67$^{SRF}$ | $^{274}$GTTSTIQTAP$^{313}$SA VSSADGTVLK$^{374}$DSS TDLTQTSSSGTVTLP | J03161 |
| Sentrinization | RanGAP1 |  | Johnson & Hochstrasser, 1997, Trends Cell. Biol. 7:408–413 |
|  | PML |  | Kamitani et al., 1998, J. Biol. Chem. 273:3117–3120 |

A simple FRET assay based upon these modifications to a site for enzymatic modification present on a binding domain, sequence, nucleic acid or polypeptide may be performed as presented below. It is contemplated that other light-based detection assays, such as those involving single labels, labels and corresponding quenchers, etc. can be employed.

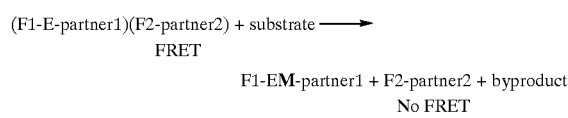

where E=modification site
M=modification
F1=donor fluorophore
F2=acceptor fluorophore Alternatively, a FRET-based assay may follow a format such as:

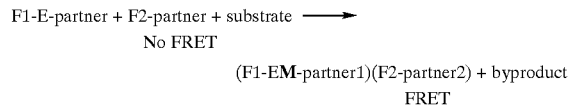

Placement of the modification site may be determined empirically (see below), such that the location itself permits the interaction between the binding domain, sequence, nucleic acid or polypeptide and a binding partner but that the association is altered on modification of the site. This change in association may be a direct or indirect consequence of modification. While not being bound to any theory, such a change may be based on, for example, a conformational or electrostatic change brought about by phosphorylation or dephosphorylation. In cases where there is no appropriate structural information, the sites for the attachment of a fluorophore or other label or quencher will also be determined empirically.

Table 4 lists enzymes which perform the several modifications discussed herein as being of use in the invention.

TABLE 4

| Modification | Enzyme | Specific Action | GenBank No./Reference |
|---|---|---|---|
| Mono-ADP-Ribosylation | NAD:Arginine ADP-ribosyl transferase |  | Zolkiewska, A., Nightingale, M. S., Moss, J., 1992, PNAS B2:11352–6 |
| Poly-ADP-Ribosylation | Drosophila PARP |  | D13806, D13807, D13808 |
| Ubiquitination | E1E2 (UBC8) E3 (RSP5) | Ubiquitination of large subunit of RNA pol II (Rpb1) (NB, E2 and E3 confer substrate specificity on the ubiquitination) | X55386, X56507 M65083 U18916, L11119, L11120, U00092, U75972 |
| N-Myristoylation | Glycylpeptide-N-tetradecanoyl-transferase (peptide N-myristoyl-transferase) |  | M86707 |
| N-Glycosylation | UDP-N-acetylglucosamine-dolichyl-phosphate N-acetyl-glucosamine phosphotransferase | Initial step in synthesis of dolichol-P-P-oligo-sacharides | X65603, S41875 |
| O-Glycosylation | O-G1cNAc transferase |  | Kreppel et al., 1997, J.Biol. Chem.272: 9308–15 |
| Sentrinization | Ubc9 |  | Gong et al., 1997 J.Biol.Chem., 272:28198–28201 |

Enzymes which modify nucleic acids, such modifications affecting the ability of the modified nucleic acid to bind to a polypeptide, may also be assayed by the methods of our invention. Such enzymes include but are not limited to, for example, methylases and demethylases. It is known that the methylation state of a nucleic acid sequence may affect the ability of a polypeptide to bind to it, as described above. Thus, it is envisaged to use our methods to detect and assay such enzymes by providing a binding domain comprising a nucleic acid sequence, together with a binding partner comprising a polypeptide sequence, such that the binding of the polypeptide to the nucleic acid is dependent on the modification state of the nucleic acid.

Epigenetic Modifications of Nucleic Acids

Various eigenetic modifications of nucleic acids are also known, for example, methylation. Methylation of DNA is an epigenetic modification that can play an important role in the control of gene expression in mammalian cells (reviewed in Momparler & Bovenzi, 2000, *J Cell Physiol*. 183(2):145–54 and Robertson & Jones, 2000, *Carcinogenesis* 21:461–467).

The enzyme involved in this process is DNA methyltransferase, which catalyzes the transfer of a methyl group from 5-adenosyl-methionine to cytosine residues to create 5-methylcytosine, a modified base that is found mostly at CpG sites in the genome. Methylation patterns are the result of de novo methylation, demethylation, and maintenance of existing methylation. It has been shown that protein binding can specify sites of demethylation through a replication-dependent pathway (Hsieh, 2000, *Curr. Opin. Genet. Dev.* 10:224–8), and a family of methyltransferases and methyl binding proteins has been identified. A mammalian DNA methyltransferase, DNMT1, is a large enzyme (about 200 kDa) composed of a C-terminal catalytic domain with homology to bacterial cytosine-5 methylases and a large N-terminal regulatory domain with several functions, including targeting to replication foci (Leonhardt et al., 1992, *Cell* 71:865–873). Several forms of DNMT1 have been detected, and targeting of DNMT1 to replication foci via the N-terminal domain is believed to allow for copying of methylation patterns from the parental to the newly synthesized daughter DNA strand (Pradhan et al., 1997, *Nucleic Acids Res.* 25:4666–4673). Another group of DNMTs, Dnmt3a and 3b, has recently been identified as candidates for de novo methyltransferases (Okano et al., 1998, *Nature Genet.* 19:219–220). Enzymatic removal of 5-methylcytosine from DNA has also been described but is less well characterized. One mechanism identified involves a 5-methylcytosine DNA glycosylase activity (Fremant et al., 1997, *Nucleic Acids Res.* 25:2375–2380). A more recent mechanism has been reported which appears to involve specific removal of the methyl group from 5-methylcytosine in the form of methanol by a single polypeptide which also contains a methyl-CpG binding motif (Bhattacharya et al., 1999, *Nature* 327:579–583).

Detailed studies of the effects of DNA methylation on promoter activity have revealed that DNA methylation is a potent suppressor of gene activity (Jones & Laird, 1999, *Nature Genet.* 21:163–166.). Two mechanisms have been proposed for this repression. The first involves the direct inhibition of binding of sequence-specific transcription factors whose binding sites contain CpG sites such as c-Myc/Myn, AP-2, E2F and ATF/CREB-like proteins binding to cAMP responsive elements (Tate & Bird, 1993, *Curr. Opin. Genet. Dev.* 3:226–231). This mechanism requires that a CpG dinucleotide be present within the binding site. The second mechanism of repression is mediated by methyl-CpG binding proteins (for example MeCP1 and MeCP2 also known as the MBD family) which are not sequence-specific but are specific for methylated DNA. Such proteins may compete with transcription factors for their binding sites in methylated DNA or reorganize DNA into tightly packed chromatin structures incompatible with transcription (Boyes & Bird, 1992, *EMBO J.* 11:327–333). Binding proteins that preferentially recognize methylated DNA then associate with histone deacetylase and chromatin remodeling complexes to cause stabilization of condensed chromatin (reviewed in Newell-Price et al., 2000, *Trends Endocrinol. Metab.* 11: 142–148). Methylation of DNA has also been shown to be essential for normal development (Li et al., 1992, *Cell* 69:915–926), X chromosome inactivation (Panning & Jaenisch, 1998, *Cell* 93:305–308), imprinting (Li et al., 1993, *Nature* 366:362–365) and suppression of parasitic DNA sequences (Walsh et al, 1998, *Nature Genet.* 20:116–117).

In different types of tumors, aberrant or accidental methylation of CpG islands in the promoter region has been observed for many cancer-related genes (for example, tumor suppressor genes, genes that suppress metastasis and angiogenesis, and genes that repair DNA) resulting in the silencing of their expression. This suggests that epigenetics plays an important role in tumorigenesis. Modulators of methylase enzyme activity are also known, for example, 5-aza-2'-deoxycytidine (5-AZA-CdR), which has been shown to reactivate the expression of many of the malignancy suppressor genes in human tumor cell lines.

A demethylase enzyme catalyzes the removal of a methyl group from 5'-methyl cytosine.

iii. Design of Binding Domains and Binding Partners Therefor for use in the Invention According to the invention, a binding domain is such that its association with a binding partner is dependent upon enzymatic modification at a site for enzymatic modification which is present in, introduced into or altered within the binding domain. As noted above, where the binding domain comprises a polypeptide, the binding partner comprises a nucleic acid, and vice versa. The binding domain may itself be a naturally-occurring amino acid sequence or may be non-natural. The location of the enzymatic modification site must be such that it is tolerated in one state of modification (for example, prior to modification), but provokes dissociation of the complex in the opposite state of modification (following modification; or vice versa). As stated above, placement of the modification site within the domain may involve empirical testing on a case-by-case basis; however, such testing can be facilitated through the use of knowledge of the structural basis of the interaction sites in the complex. Such knowledge may be structural (e.g., using crystallographic data or a molecular modeling algorithm of the 3-dimensional structure of the protein or proteins involved in the complex of interest), a functional assessment of the regions of primary sequence important in binding, or a combination of these. These data will identify regions of the protein or nucleic acid most likely to be influenced by the insertion of a enzymatic modification site.

The contact face between components of the complex is one location at which a site for enzymatic modification might be engineered, but it is not the only useful location. The modification of a site remote from the interface site(s) can also lead to binding or dissociation of the complex. This would be expected to occur upon long-range alterations in structure as a consequence of the enzymatic modification, which could be as extreme, for example, as structural collapse following modification.

A peptide, PK.T (5–24 amide), derived from a protein inhibitor of the cAMP-dependent protein kinase binds to the active site of protein kinase A (PKA) with high affinity. The 3-D structure of this complex is known (Knighton et al., 1991, *Science* 253:414–420) as is a functional dissection of the sequence of this peptide to identify residues involved in this biological activity (Glass et al., 1989, *J. Biol. Chem.* 264:8802–8810). The binding of PKI(5–24 amide) to the catalytic subunit of PKA can be monitored by a number of techniques including FRET, fluorescence correlation spectroscopy (FCS) or fluorescence anisotropy provided both components in the former case or the PKI(5–24 amide) component in the latter two cases, respectively, are labeled with appropriate fluorophores.

The introduction of a PKA phosphorylation site into this peptide, by mutation of Ala$^{21}$Ser (called PKT (A21S) hereinafter), results in a reporter molecule for protein kinase A activity. When used in an assay of the invention, PKI (A21S) binds to PKA when dephosphorylated, but dissociates from the enzyme once phosphorylated.

In some instances the binding partner might require mutation of its primary sequence to accommodate the enzymatic modification site introduced into the engineered binding domain.

Molecular Methods Useful in Producing an Engineered Binding Domain

An engineered binding domain of use in the invention is produced using molecular methods such as are known in the art (see, for example, Sambrook et al., 1989, *Molecular Cloning. A Laboratory Manual*, 2nd Edition, Cold Spring Harbor Laboratory Press, Cold Spring Harbor, N.Y.; Ausubel et al., *Current Protocols in Molecular Biology*, copyright 1987–1994, *Current Protocols*, copyright 1994–1998, John Wiley & Sons, Inc.). Such methods include chemical synthesis of a polypeptide sequence that encompasses an engineered binding domain or expression of a recombinant polynucleotide encoding such a molecule. Such a polynucleotide may be chemically synthesized; however, of particular use in the invention are methods of in vitro or otherwise site-directed mutagenesis by which to engineer a site for enzymatic modification into an existing binding domain (whether natural or previously engineered) or by which to alter the enzyme specificity of an existing site.

Typically, methods for in vitro mutagenesis comprise the annealing of a mutagenic oligonucleotide primer comprising the desired alteration to a complementary, single-stranded template, followed by second strand synthesis, whether using single-cycle synthesis or polymerase chain reaction (PCR). Cloning and sequencing are then performed to identify and isolate molecules bearing the desired alterations. Such mutagenesis methods optionally include a selection for mutated molecules, either through the use of modified nucleotides incorporated into the nascent polynucleotide strand or through the incorporation of a restriction site into the vector bearing the first strand which is disrupted in the second strand (i.e., in coupled priming; Carter et al., 1985, *Nucleic Acids Res*. 13:4431–4443) and, with either technique, subsequent transformation of the first and second strands into a strain of host cells that selectively destroys the first strand and propagates the second.

Kits and individual components for in vitro mutagenesis enjoy wide commercial availability. A non-limiting sampling of such kits is as follows:

From Stratagene (Lajolla, Calif., U.S.A.): ExSite PCR-Based Site-Directed Mutagenesis Kit (catalog number: 200502), QuikChange Site-Directed Mutagenesis Kit (catalog number: 200518), Chameleon Double-Stranded, Site-Directed Mutagenesis Kit (catalog numbers: 200508 and 200509)

From Promega (Madison, Wis., U.S.A.): Interchange in vivo Amber Suppressor Mutagenesis System (catalog number: Q5080), Altered Sites II in vitro Mutagenesis Systems (catalog numbers: Q6210, Q6090 and Q6080), GeneEditor in vitro Site-Directed Mutagenesis System (catalog number: Q9280), Erase-a-Base System (catalog numbers E5850 and E5750)

From New England Biolabs (Beverly, Mass., U.S.A.): Code20 Cassette Mutagenesis System (catalog number: 7520)

All such kits are used according to the manufacturer's instructions.

iv. Selection-of Functional Partners Sensitive to Post-translation Modification

An engineered binding domain generated as described above may then be assayed for modification-dependent binding to a binding partner with which it was known to associate prior to engineering or; if binding of the engineered binding domain and the binding partner is determined to be modification-sensitive (i.e., such that the engineered binding domain and the binding partner either do- or do not associate, depending upon modification of the engineered site), the engineered binding domain and binding partner (or pair of binding partners) are useful in assays of enzymatic activity according to the invention.

Alternatively, candidate binding partners can be screened for their ability to bind the engineered binding domain in a modification-dependent manner. Such binding partners may be selected or designed based upon sequence homology with known binding partners or on molecular modeling data (e.g., from a modeling algorithm). Potential binding partners additionally may be purified (e.g., using the modified engineered binding domain as the trap in affinity chromatography or as a probe for a library) from a population of polypeptide molecules. A library from which to draw a diverse population of polypeptide sequences of use in the invention includes, but is not limited to, an expression library or a synthetic peptide library (see "Candidate modulators" below).

One library-based technique which is useful in the invention to generate new pairs of assay components is that of phage display, which provides convenient testing of polypeptide sequences able to complex with the target sequence from a vast repertoire of different polypeptide sequences.

Filamentous bacteriophage display a small number of copies of a protein termed g3p on their surface. This protein is responsible for interacting with proteins on the surface of *Escherichia coli* and facilitates the infection of the bacterium. This protein possesses three globular domains linked by protease resistant, flexible amino acid sequences. The g3p protein can be modified to provide a means of presenting protein structures from which proteins capable of forming a stable binding complex can be identified. Such a bioassay can be configured by, for example, expression of the test proteins as an extension of the g3p sequence. Proteins able to bind with target nucleic acid A can be selected by affinity purification on a matrix displaying nucleic acid A.

If A is engineered to introduce a site for enzymatic modification, then binding partners tolerant of that engineered site can be identified. A second round of selection can then be undertaken to identify the binding partners which dissociate upon enzymatic modification of that site (i.e., those to which binding of the engineered binding domain is dependent upon enzymatic modification).

Methods by which assays of the invention are performed using the binding domains and binding partners therefor produced as described above are described in detail in the following sections and in the Example.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., *Molecular Cloning A Laboratory Manual*, $2^{nd}$ Edition (1989) Cold Spring Harbor Laboratory Press, Cold Spring Harbor, N.Y., which is incorporated herein by reference), chemical methods, pharmaceutical formulation and delivery and treatment of patients.

B. Methods to Detect Protein:nucleic Acid Binding According to the Invention

According to the invention, the activity of a modifying enzyme is assayed by measuring the formation or destruction of protein:nucleic complexes when the modifying enzyme is present with a binding domain, sequence or polynucleotide or polypeptide and its corresponding binding partner under conditions which permit modifying activity. The assay may be conducted such that both binding entities (i.e., nucleic acid and protein) are in solution. Alternatively, either the nucleic acid or the protein may be immobilized and the other of the nucleic acid and protein kept in solution.

By an immobilized entity, we mean one which is bound to a solid phase support. This binding may be covalent or via ionic bonding, hydrogen bonding, van-der-waals forces or any other non-covalent attachment, including antibody-antigen attachment, Ni-NTA attachment, avian-biotin pairing and the use of GST tags. The solid phase may be a membrane, for example supported nitrocellulose, a bead, for example an agarose, glass or Sepharose bead, a magnetic bead, a plastic substrate such as an ELISA dish or other plate, or may be a BIAcore chip or other silicon based chip. Preferably, the polypeptide or nucleic acid is bound to the support in such a way that it is at least partly free in solution. A polypeptide may be bound to the support via an N- or C-terminal linkage, for example via a C-terminal cysteine residue. Various other means of immobilization are known in the art, for example, by exposing biotin labeled binding entities (such as biotin labeled proteins or biotin labeled nucleic acids) to streptavidin coated beads (Dynal).

Methods which enable the detection of protein:nucleic acid complexes (i.e., methods which allow one of skill in the art to discriminate between pairing partners which are bound and those which are unbound) are known in the art. Of particular use in the invention are those methods which entail fluorescent labeling of the binding domain, sequence, nucleic acid or polypeptide and/or its binding partner, and subsequent detection of changes in fluorescence, whether in frequency or level, following incubation of the labeled assay components with the candidate modifying enzyme. Several such procedures are briefly summarized below.

Fluorescent Resonance Energy Transfer (FRET)

A tool with which to assess the distance between one molecule and another (whether protein or nucleic acid) or between two positions on the same molecule is provided by the technique of fluorescent resonance energy transfer (FRET), which is now widely known in the art (for a review, see Matyus, 1992, *LI. Photochem. Photobiol. B:Biol.* 12:323–337, which is herein incorporated by reference). FRET is a radiationless process in which energy is transferred from an excited donor molecule to an acceptor molecule; the efficiency of this transfer is dependent upon the distance between the donor and acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, *Principles of Fluorescence Spectroscopy*, Plenum Press, New York; Jovin & Jovin, 1989, *Cell Structure and Function by Microspectrofluorometry*, eds. E. Kohen & J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled either in vivo or in vitro by methods known in the art. According to the invention, a binding domain, sequence, nucleic acid or polypeptide and its corresponding binding partner are differentially labeled, one with a donor and the other with an acceptor label, and differences in fluorescence between a test assay, comprising a modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent labels (e.g., fluorescent proteins as described below or the fluorophores rhodamine, fluorescein, SPQ, and others as are known in the art) or a fluorescent label and a molecule known to quench its signal; differences in the proximity of the binding domain, sequence, nucleic acid or polypeptide and the binding partner with and without the protein- or nucleic acid-modifying enzyme can be gauged based upon a difference in the fluorescence spectrum or intensity observed.

This combination of labeling methods and devices confers a distinct advantage over prior art methods for determining the activity of modifying enzymes, as described above, in that results of all measurements are observed in real time (i.e., as a reaction progresses). This is significantly advantageous, as it allows both for rapid data collection and yields information regarding reaction kinetics under various conditions.

A sample, whether in vitro or in vivo, assayed according to the invention therefore comprises a mixture at equilibrium comprising at least one labeled binding domain, sequence, nucleic acid or polypeptide and its corresponding binding partner which, when disassociated from one another, fluoresce at one frequency and, when complexed together, fluoresce at another frequency or, alternatively, of molecules which either do or do not fluoresce depending upon whether or not they are associated.

A fluorescent label is either attached to the surface of the binding domain, sequence, nucleic acid or polypeptide or binding partner therefor or, alternatively, a fluorescent protein is fused or conjugated to the binding domain, sequence, nucleic acid or polypeptide or binding partner therefor, as described below. The choice of fluorescent label will be such that upon excitation with light, labeled molecules which are associated will show optimal energy transfer between fluorophores. In the presence of a modifying enzyme (e.g., a methylating-, phosphorylating-, a dephosphorylating-, a ubiquitinating-, ADP-ribosylating-, sentrinizing, prenylating- or glycosylating enzyme), a complex comprising a binding domain, sequence, nucleic acid or polypeptides and its binding partner dissociates due to structural or electrostatic disruption which occurs as a consequence of modification of the enzyme recognition site, thereby leading to a decrease in energy transfer and increased emission of light by the donor fluorophore. In this way, the state of modification can be monitored and quantitated in real-time.

As used herein, the term "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 4.

TABLE 44

| Fluorophore | Excitation (nm) | Emission (nm) | Color |
| --- | --- | --- | --- |
| PKH2. | 490 | 504 | green |
| PKH67r | 490 | 502 | green |
| Fluorescein (FITC) | 495 | 525 | green |
| Hoechst 33258 | 360 | 470 | blue |
| R-Phycoerytbrin (PE) | 488 | 578 | orange-red |
| Rhodamine (TRITC) | 552 | 570 | red |
| Quantum Red | 488 | 670 | red |
| PKH26 | 551 | 567 | red |
| Texas Red | 596 | 620 | red |
| Cy3 | 552 | 570 | red |

It should also be noted that where the fluorescent technique used requires both a donor molecule and an acceptor molecule, naturally occurring or engineered tryptophan residues within the binding domain and/or partner are suitable as a donor and therefore in this situation, only one of the molecules need be labeled with a fluorescent molecule.

Examples of fluorescent proteins which vary among themselves in excitation and emission maxima are listed in Table 1 of WO 97/28261 (Tsien et al., 1997, supra). These (each followed by [excitation max./emission max.] wavelengths expressed in nanometers) include wild-type Green Fluorescent Protein [395(475)1508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L[484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the GenBank and SwissProt public databases. Further examples are described in Matz et al, 1999, Nature Biotech. 17:969–973) and include red fluorescent protein from Discosoma sp. (drFPS83).

A number of parameters of fluorescence output are envisaged including:

1) measuring fluorescence emitted at the emission wavelength of the acceptor (A) and donor (D) and determining the extent of energy transfer by the ratio of their emission amplitudes;

2) measuring the fluorescence lifetime of D;
3) measuring the rate of photobleaching of D;
4) measuring the anistropy of D and/or A; or
5) measuring the Stokes shift monomer; excimer fluorescence.

Certain of these techniques are presented below.

Alternative Fluorescent Techniques Suitable for Monitoring Protein:nucleic Acid Binding in Assays of the Invention One embodiment of the technology utilizes monomer:excimer fluorescence as the output. The fluorophore pyrene when present as a single copy displays fluorescent emission of a particular wavelength significantly shorter than when two copies of pyrene form a planar dimer (excimer). As above, excitation at a single wavelength (probably 340 nm) is used to review the excimer fluorescence (~470 nm) over monomer fluorescence (~375 nm) to quantify assembly:disassembly of the reporter molecule.

Additional embodiments of the present invention are not dependent on FRET. For example the invention can make use of fluorescence correlation spectroscopy (FCS), which relies on the measurement of the rate of diffusion of a label (see Elson & Magde, 1974, Biopolymers 13:1–27; Rigler et al., 1992, in Fluorescence Spectroscopy: New Methods and Applications, Springer Verlag, pp.13–24; Eigen & Rigler, 1994, Proc. Natl. Acad. Sci. U.S.A. 91:5740–5747; Kinjo & Rigler, 1995, Nucleic Acids Res. 23:1795–1799).

In FCS, a focused laser beam illuminates a very small volume of solution, of the order of $10^{15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide or nucleic acid will diffuse at a slower rate if it is large than if it is small. Thus, polypeptide:nucleic acid complexes will display slow diffusion rates, resulting in a lower number of fluorescent bursts in any given timeframe, while labeled polypeptides or nucleic acids which are not multimerized or which have dissociated from a multimer will diffuse more rapidly. Binding can be calculated directly from the diffusion rates through the illuminated volume.

Where FCS is employed, rather than FRET, it is not necessary to label more than one member of the pair. Preferably, a single polypeptide or nucleic acid member of the multimer is labeled. The labeled member dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, Principles of Fluorescence Spectroscopy, Plenum Press, New York, incorporated herein by reference (see, for example, page 167).

Fluorescence anisotropy relies on the measurement of the rotation of fluorescent groups. Larger complexes rotate more slowly than single molecules, allowing the formation of complexes to be monitored.

Fluorescent Protein Labels in Assays of the Invention

In a FRET assay of the invention, the fluorescent protein labels are chosen such that the excitation spectrum of one of the labels (the acceptor) overlaps with the emission spectrum of the excited fluorescent label (the donor). The donor is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and reemission of fluorescent light at the longer wavelengths (lower energies) characteristic of the acceptor. When the donor and acceptor labels become spatially separated, FRET is diminished or eliminated.

One can take advantage of the FRET exhibited by a binding domain, sequence, nucleic acid or polypeptide and its corresponding binding partner labeled with different fluorescent protein labels, wherein one is linked to a donor and the other to an acceptor label, in monitoring enzymatic modification according to the present invention. For example, two distinct polypeptides, ("single" fusion proteins) one comprising a binding domain, sequence, nucleic acid or polypeptide and the other its corresponding binding partner, may be differentially labeled with the donor and acceptor fluorescent protein labels, respectively. Where the binding domain is a polypeptide, the labeled binding domains, sequences or polypeptides may be produced via the expression of recombinant nucleic acid molecules comprising an in-frame fusion of sequences encoding a binding domain, sequence, or polypeptide and a fluorescent protein label either in vitro (e.g., using a cell-free transcription/translation system, as described below, or instead using cultured cells transformed or transfected using methods well known in the art) or in vivo, for example in a trangenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired.

The means by which the association between a binding domain, sequence, nucleic acid or polypeptide and its binding partner is assayed using fluorescent protein labels according to the invention may be briefly summarized as follows:

One of the binding domain, sequence, nucleic acid or polypeptide and its binding partner is labeled with a green fluorescent protein, while the other is preferably labeled with a red or, alternatively, a blue fluorescent protein. Useful donor:acceptor pairs of fluorescent proteins (see Tsien et al., 1997, supra) include, but are not limited to:

Donor: S72A, K79R, Y145F, M153A and T203I (excitation λ 395 nm; emission λ 511)

Acceptor: S65G, S72A, K79R and T203Y (excitation λ 514 nm; emission λ 527), or T203Y/S65G, V68L, Q69K or S72A (excitation λ 515 nm; emission λ 527 nm).

An example of a blue:green pairing is P4–3 (shown in Table 1 of Tsien et al., 1997, supra) as the donor label and S65C (also of Table 1 of Tsien et al., 1997, supra) as the acceptor label. The mixtures comprising binding domains, sequences or polypeptides and their corresponding binding partners are exposed to light at, for example, 368 nm, a wavelength that is near the excitation maximum of P4–3. This wavelength excites S65C only minimally. Upon excitation, some portion of the energy absorbed by the blue fluorescent protein label is transferred to the acceptor label through FRET if the binding domain, sequence, nucleic acid or polypeptide and its corresponding binding partner are in close association. As a result of this quenching, the blue fluorescent light emitted by the blue fluorescent protein is less bright than would be expected if the blue fluorescent protein existed in isolation. The acceptor label (S65C) may re-emit the energy at longer wavelength, in this case; green fluorescent light.

After modification (e.g., phosphorylation, ADP-ribosylation, ubiquitination, prenylation, sentrination or glycosylation, all as described below) of the binding domain, sequence, nucleic acid or polypeptide by an enzyme, the two (and, hence, the green and red or, less preferably, green and blue fluorescent proteins) physically separate or associate, accordingly inhibiting or promoting FRET. For example, if activity of the modifying enzyme results in dissociation of a protein:nucleic acid dimer, the intensity of visible blue fluorescent light emitted by the blue fluorescent protein increases, while the intensity of visible green light emitted by the green fluorescent protein as a result of FRET, decreases.

Such a system is useful to monitor the activity of enzymes that modify the binding domain, sequence, nucleic acid or polypeptide or binding partner to which the fluorescent protein labels are bound as well as the activity of modulators or candidate modulators of those enzymes.

In particular, this invention contemplates assays in which the amount- or activity of a modifying enzyme in a sample is determined by contacting the sample with an binding domain, sequence, nucleic acid or polypeptide and its binding partner, differentially labeled with fluorescent proteins, as described above, and measuring changes in fluorescence of the donor label, the acceptor label or the relative fluorescence of both.

Alternatively, in single-label assays of the invention, whether involving use of a chemical fluorophore or a single fluorescent fusion construct, a non-fluorescent quencher may be used. Thus, the enzyme's substrate, i.e., the binding domain, sequence, nucleic acid or polypeptide comprising a enzymatic modification site and product (i.e., the binding domain, sequence, nucleic acid or polypeptide and its binding partner after addition or removal of a chemical moiety to/from the modification site) are both fluorescent, but with different fluorescent characteristics.

In particular, the substrate and modified products exhibit different ratios between the amount of light emitted by the donor and acceptor labels. Therefore, the ratio between the two fluorescences provides an indication of the degree of conversion of substrate to products, independent of the absolute amount of either, the thickness or optical density of the sample, the brightness of the excitation lamp, the sensitivity of the detector, etc. Furthermore, Aequorea-derived or -related fluorescent protein labels tend to be protease resistant. Therefore, they are likely to retain their fluorescent properties throughout the course of an experiment.

Protein Fusion Constructs According to the Invention

As stated above, recombinant nucleic acid constructs of particular use in the invention include those which comprise in-frame fusions of sequences encoding a binding domain, sequence or polypeptide and a fluorescent protein. Such a nucleic acid molecule encodes a polypeptide comprising a binding domain, sequence or polypeptide fused either to a donor or acceptor fluorescent protein label and operatively linked to gene regulatory sequences.

"Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

As described above, a donor fluorescent protein label is capable of absorbing a photon and transferring energy to another fluorescent label. The acceptor fluorescent protein label is capable of absorbing energy and emitting a photon. Alternatively, a fluorophore emits fluorescent light which is absorbed by a quencher. If needed, the linker connects the binding domain, sequence or polypeptide either directly, or indirectly through an intermediary linkage, with one or both of the donor and acceptor fluorescent protein labels or the fluorescent label and, optionally, the quencher if a non-FRET assay is being performed. Regardless of the relative order of the binding domain, sequence or polyepeptide or its binding partner and the donor and acceptor fluorescent protein labels on a polypeptide molecule, it is essential that sufficient distance be placed between the donor and acceptor or the fluorescent label and corresponding quencher by the linker and/or the binding domain, sequence, nucleic acid or polypeptide and corresponding binding partner to ensure that FRET does not occur unless the binding domain, sequence or polypeptide and its binding partner bind. It is desirable, as described in greater detail in WO97/28261, to select a donor fluorescent protein label with an emission spectrum that overlaps with the excitation spectrum of an acceptor fluorescent protein label. In some embodiments of the invention the overlap in emission and excitation spectra will facilitate FRET. A fluorescent protein of use in the invention includes, in addition to those with intrinsic fluorescent properties, proteins that fluoresce due to intramolecular rearrangements or the addition of cofactors that promote fluorescence.

For example, green fluorescent proteins (GFPs) of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium* (Ward et al., 1982, *Photochem. Photobiol.* 35:803–808; Levine et al., 1982, *Comp. Biochem. Physiol.* 72B:77–85).

A variety of Aequorea-related GFPs having useful excitation and emission spectra have been engineered by modifying the amino acid sequence of a naturally-occurring GFP from *Aequorea victoria* (Prasher et al., 1992, *Gene* 111:229–233; Heim et al., 1994, *Proc. Natl. Acad, Sci. U.S.A.* 91:12501–12504; PCTUS95/14692). As used herein, a fluorescent protein is an Aequorea-related fluorescent protein if any contiguous sequence of 150 amino acids of the fluorescent protein has at least 85% sequence identity with an amino acid sequence, either contiguous or non-contiguous, from the wild-type Aequorea green fluorescent protein (SwissProt Accession No. P42212). Similarly, the fluorescent protein may be related to Renilla or Phialidium wild-type fluorescent proteins using the same standards.

Aequorea-related fluorescent proteins include, for example, wild-type (native) *Aequorea victoria* GFP, whose nucleotide and deduced amino acid sequences are presented in GenBank Accession Nos. L29345; M62654, M62653 and others Aequorea-related engineered versions of Green Fluorescent Protein, of which some are listed above. Several of these, i.e., P4, P4–3, W7 and W2 fluoresce at a distinctly shorter wavelength than wild type.

Recombinant nucleic acid molecules encoding single- or tandem fluorescent protein/polypeptide comprising engineered binding domain, sequences or polypeptides or their binding partners useful in the invention may be expressed for in vivo assay of the activity of a modifying enzyme on the encoded products. Alternatively, the encoded fusion proteins may be isolated prior to assay, and instead assayed in a cell-free in vitro assay system, as described elsewhere herein.

C. Methods for Detection of Protein Modification in Real Time i. In vitro Protein Modification and Detection Thereof
Modifying Enzymes The invention requires the presence of a modifying enzyme which catalyzes either the addition or removal of a modifying group. A range of kinases, phosphatases and other modifying enzymes are available commercially (e.g., from Sigma, St. Louis, Mo.; Promega, Madison, Wis.; Boehringer Mannheim Biochemicals, Indianapolis, Ind.; New England Biolabs, Beverly, Mass.; and others). Alternatively, such enzymes may be prepared in the laboratory by methods well known in the art.

The catalytic sub-unit of protein kinase A (c-PKA) can be purified from natural sources (e.g., bovine heart) or from cells/organisms engineered to heterologously express the enzyme. Other isoforms of this enzyme may be obtained by these procedures. Purification is performed as previously described from bovine heart (Peters et al., 1977, *Biochemistry* 16:5691–5697) or from a heterologous source (Tsien et al., WO92/00388), and is in each case briefly summarized as follows:

Bovine ventricular cardiac muscle (2 kg) is homogenized and then centrifuged. The supenatant is applied to a strong anion exchange resin (e.g., Q resin, Bio-Rad) equilibrated in a buffer containing 50 mM Tris-HCl, 10 mM NaCl, 4 mM EDTA pH 7.6 and 0.2 mM 2-mercaptoethanol. The protein is eluted from the resin in a second buffer containing 50 mM Tris-HCl, 4 mM EDTA pH 7.6, 0.2 mM 2-mercaptoethanol, 0.5M NaCl. Fractions containing c-PKA are pooled and ammonium sulphate added to 30% saturation. Proteins precipitated by this are removed by centrifugation and the ammonium sulphate concentration of the supernatant was increased to 75% saturation. Insoluble proteins are collected by centrifugation (included c-PKA) and are dissolved in 30 mM phosphate buffer pH 7.0, 1 mM EDTA, 0.2 mM 2-mercaptoethanol. These proteins are then dialysed against the same buffer (500 volume excess) at 4 degrees C. for two periods of 8 hours each. The pH of the sample is reduced to 6.1 by addition of phosphoric acid, and the sample is mixed sequentially with 5 batches of CM-Sepharose (Pharmacia, ~80 ml resin each) equilibrated in 30 mM phosphate pH 6.1, 1 mM EDTA, 0.2 mM 2-mercaptoethanol. Cyclic AMP (10 $\mu$M) is added to the material which fails to bind to the CM-Sepharose, and the sample-cAMP mix is incubated with a fresh resin of CM-Sepharose (~100 ml) equilibrated as before. c-PKA is eluted from this column following extensive washing in equilibration buffer by addition of 30 mM phosphate pH 6.1, 1 mM EDTA, 1M KCl, 0.2 mM 2-mercaptoethanol. Fractions containing c-PKA are pooled and concentrated by filtration through a PM-30 membrane (or similar). The c-PKA sample is then subjected to gel-filtration chromatography on a resin such as Sephacryl 200 HR (Pharmacia).

The purification of recombinant c-PKA is as described in WO92/00388. General methods of preparing pure and partially-purified recombinant proteins, as well as crude cellular extracts comprising such proteins, are well known in the art. Molecular methods useful in the production of recombinant proteins, whether such proteins are the enzymes to be assayed according to the invention or the labeled reporter binding domains, sequences or polypeptides of the invention or their corresponding binding partners, are well known in the art (for methods of cloning, expression of cloned genes and protein purification, see Sambrook et al., 1989, supra; Ausubel et al., 1987–94, supra). The sequences of the catalytic subunit of several PKA molecules are found in the GenBank database (see PKA C, bovine, GenBank Accession Nos. X67154 and S49260; PKA Cβ1, bovine, GenBank Accession No. J02647; PKA Cβ2, bovine, M60482, the form most likely purified from bovine heart by the protocol described above).

Assays of the activity of protein- or nucleic acid-modifying enzymes may be performed using crude cellular extracts, whether to test the activity of a recombinant protein or one which is found in nature, such as in a biological sample obtained from a test cell line or animal or from a clinical patient. In the former case, use of a crude cell extract enables rapid screening of many samples, which potentially finds special application in high-throughput screening methods, e.g., of candidate modulators of protein- or nucleic acid-modifying enzyme activity. In the latter case, use of a crude extract with the labeled reporter polypeptide comprising a binding domain, sequence, nucleic acid or polypeptide of the invention and a binding partner therefor facilitates easy and rapid assessment of the activity of an enzyme of interest in a diagnostic procedure, e.g., one which is directed at determining whether a protein- or nucleic acid-modifying enzyme is active at an a physiologically-appropriate level, or in a procedure designed to assess the efficacy of a therapy aimed at modulating the activity of a particular enzyme.

Production of Polypeptides of use in the Invention

Polypeptides, a binding domain or sequence (each of which may be natural or engineered) or binding partners for such species may be synthesized by Fmoc or Thoc chemistry according to methods known in the art (e.g., see Atherton et al., 1981, *J. Chem. Soc. Perkin I* 1981(2):538–546; Merrifield, 1963, *J. Am. Chem. Soc.* 85:2149–2154, respectively). Following deprotection and cleavage from the resin, peptides are desalted by gel filtration chromatography and analyzed by mass spectroscopy, HPLC, Edman degradation and/or other methods as are known in the art for protein sequencing using standard methodologies.

Alternatively, nucleic acid sequences encoding such peptides may be expressed either in cells or in an in vitro transcription/translation system (see below) and, as with enzymes to be assayed according to the invention, the proteins purified by methods well known in the art.

Of particular use in the invention is phage display, in which an engineered binding domain is expressed from a phage chromosome along with a library of candidate binding partners. If a candidate binding partner binds the engineered binding domain, both are incorporated into the phage capsid.

Labeling Polypeptides with Fluorophores

Polypeptides, polypeptides comprising binding domains or sequences, or binding partners therefor may be labeled with thiol reactive derivatives of fluorescein and tetramethylrhodamine (isothiocyanate or iodoacetamide derivatives, Molecular Probes, Eugene, Oreg., USA) using procedures described by Hermanson G. T., 1995, *Bioconjugate Techniques*, Academic Press, London. Alternatively, primary-amine-directed conjugation reactions can be used to label lysine sidechains or the free peptide N-terminus (Hermason, 1995, supra).

Purification of Fluorescent Peptides

Fluorescent peptides are separated from unreacted fluorophores by gel filtration chromatography or reverse phase HPLC.

Synthesis of Nucleic Acid Binding Partners

Synthesis of oligonucleotides is a common practice with many companies offering commercial synthesis of oligonucleotides typically ranging in length from 10–110 bases (e.g., Sigma Genosys, London Rd, Pampisford, Cambridge, UK). A wide range of fluorophores may be added to either the 3' or 5' terminus of the oligonucleotide at the time of synthesis. Possible immobilization reagents such as Biotin may also be added to either the 3' or 5' terminus during synthesis. Synthesis produces single stranded nucleic acid which would then be annealed to its complimentary strand using the following method.

Annealing Buffer: 10 mM Tris, pH 7.5–8.0, 50 mM NaCl, 1 mM EDTA

1× TE Buffer: 10 mM Tris, pH 7.5–8.0, 1 mM EDTA

Annealing the Oligonucleotides: Mix equal volumes of both complementary oligos (at equimolar concentration) in a 1.5 ml microfuge tube. Place tube in a standard heatblock at 90–95° C. Remove the heatblock from the apparatus and allow to cool to room temperature (or at least below 30° C.) on the workbench. Slow cooling to room temperature should take 45–60 minutes. Store on ice or at 4° C. until ready to use. An alternative procedure for annealing involves the use of a thermal cycler. Dispense 100 µl aliquots of the mixed oligos into PCR tubes (500 µl size). Do not overlay the samples with oil. Place the tubes in a thermal cycler and set up a program to perform the following profile: (i) heat to 95° C. and remain at 95° C. for 2 minutes, (ii) ramp cool to 25° C. over a period of 45 minutes, (iii) proceed to a storage temperature of 4° C. Briefly spin the tubes in a microfuge to thaw all moisture from the lid. Pool samples into a larger tube, store on ice or at 4° C. until ready to use.

Phosphorylation of Binding Domains and Binding Partners In vitro

Peptides (0.01–1.0 µM) are phosphorylated by purified c-PKA in 50 mM Histidine buffer pH 7.0, 5 mM $MgSO_{4}$, 1 mM EGTA, 0.1–1.0 µM c-PKA, and 0.2 mM [$^{32}P$] γ-ATP (specific activity ~2Bq/pmol) at 30–37 degrees C. for periods of time ranging from 0 to 60 minutes. Where the chemistry of the peptide is appropriate (i.e. having a basic charge) the phosphopeptide is captured on a cation exchange filter paper (e.g., phosphocellulose P81 paper; Whatman), and reactants are removed by extensive washing in 1% phosphoric acid (see Casnellie, 1991, *Methods Enzymol.* 200:115–120). Alternatively, phosphorylation of samples is terminated by the addition of SDS-sample buffer (Laemmli, 1970, *Nature* 227:680–685) and the samples analyzed by SDS-PAGE electrophoresis, autoradiography and scintillation counting of gel pieces.

Dephosphorylation of Binding Domains and Binding Partners In vitro

The dephosphorylation of peptides phosphorylated as above is studied by removal of ATP (through the addition of 10 mM glucose and 30 U/ml hexokinase; Sigma, St. Louis, Mo.) and addition of protein phosphatase-1 (Sigma). Dephosphorylation is followed at 30–37 degrees C. by quantitation of the remaining phosphopeptide component at various time points, determined as above.

Fluorescence Measurements of Protein Modification In vitro in Real Time

Donor and acceptor fluorophore-labeled binding polypeptides or polypeptides comprising binding domains or sequences and the corresponding binding partners for any such molecules (molar equivalents of fluorophore-labeled polypeptide or molar excess of acceptor-labeled polypeptide) are first mixed. Samples are analyzed in a fluorimeter using excitation wavelengths relevant to the donor fluorescent label and emission wavelengths relevant to both the donor and acceptor labels. A ratio of emission from the acceptor over that from the donor following excitation at a single wavelength is used to determine the efficiency of fluorescence energy transfer between fluorophores, and hence their spatial proximity. Typically, measurements are performed at 0–37 degrees C. as a function of time following the addition of the modifying enzyme (and, optionally, a modulator or candidate modulator of function for that enzyme, as described below) to the system in 50 mM histidine pH 7.0, 120 mM KCl, 5 mM $MgSO_4$, 5 mM NaF, 0.05 mM EGTA and 0.2 mM ATP. The assay may be performed at a higher temperature if that temperature is compatible with the enzyme(s) under study.

Alternative Cell-free Assay System of the Invention

A cell-free assay system must permit binding of a binding domain, sequence, nucleic acid or polypeptide with its binding partner to occur in a modification-dependent manner. As indicated herein, such a system may comprise a low-ionic-strength buffer (e.g., physiological salt, such as simple saline or phosphate- and/or Tris-buffered saline or other as described above), a cell culture medium, of which many are known in the art, or a whole or fractionated cell lysate. The components of an assay of enzymatic modification of a polypeptide molecule according to the invention may be added into a buffer, medium or lysate or may have been expressed in cells from which a lysate is derived. Alternatively, a cell-free transcription- and/or translation system may be used to deliver one or more of these components to the assay system. Nucleic acids of use in cell-free expression systems according to the invention are as described for in vivo assays, below.

An assay of the invention may be performed in a standard in vitro transcription/translation system under conditions which permit expression of a recombinant or other gene. The TNT T7 Quick Coupled Transcription/Translation System (Cat. #L1170; Promega) contains all reagents necessary for in vitro transcription/translation except the DNA of interest and the detection label; as discussed below, binding domains, sequences or polypeptides or their binding partners may be encoded by expression constructs in which their coding sequences are fused in-frame to those encoding fluorescent proteins. The TNT Coupled Reticulocyte Lysate Systems (comprising a rabbit reticulocyte lysate) include: TNT T3 Coupled Reticulocyte Lysate System (Cat. #L4950; Promega); TNT T7 Coupled Reticulocyte Lysate System (Cat. #L4610; Promega); TNT SP6 Coupled Reticulocyte Lysate System (Cat. #L4600; Promega); NT T7/SP6 Coupled Reticulocyte Lysate System (Cat. #L5020; Promega); TNT T7/T3 Coupled Reticulocyte Lysate System (Cat. #L5010; Promega).

An assay involving a cell lysate or a whole cell (see below) may be performed in a cell lysate or whole cell preferably eukaryotic in nature (such as yeast, fungi, insect, e.g., Drosophila, mouse, or human). An assay in which a cell lysate is used is performed in a standard in vitro system under conditions which permit gene expression. A rabbit reticulocyte lysate alone is also available from Promega, either nuclease-treated (Cat. #L4960) or untreated (Cat. #L4151).

Candidate Modulators of Protein- or Nucleic Acid-modifying Enzymes to be Screened According to the Invention Whether in vitro or in an in vivo system (see below), the invention encompasses methods by which to screen compositions which may enhance, inhibit or not affect (e.g., in a cross-screening procedure in which the goal is to determine whether an agent intended for one purpose additionally affects general cellular functions, of which protein modification is an example) the activity of a protein- or nucleic acid-modifying enzyme.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from, e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 500 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g., for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target mRNA. Ribozymes of the hammerhead class are the smallest known, and lend themselves both to in vitro production and delivery to cells (summarized by Sullivan, 1994, *J. Invest. Dermatol.* 103:85S–98S; Usman et al., 1996, *Curr. Opin. Struct. Biol.* 6:527–533).

As stated above, antibodies are of use in the invention as modulators (specifically, as inhibitors) of protein- or nucleic acid-modifying enzymes. Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g., by fusion with an immortalizing fusion partner) to produce monoclonal antibodies.

1. Polyclonal Antibodies

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.* 267:4815–4823). The serum is titered against protein antigen by ELISA (below) or alternatively by dot or spot blotting (Boersma & Van Leeuwen, 1994, *J. Neurosci. Methods* 51:317). At the same time, the antiserum may be used in tissue sections prepared as described below. The serum is shown to react strongly with the appropriate peptides by ELISA, for example, following the procedures of Green et al., 1982, *Cell* 28:477–487.

2. Monoclonal Antibodies

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature* 294:278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Determination of Activity of Candidate Modulator of a Protein- or Nucleic Acid-modifying Enzyme A candidate modulator of the activity of a protein- or nucleic acid-modifying enzyme may be assayed according to the invention as described herein, is determined to be effective if its use results in a difference of about 10% or greater relative to controls in which it is not present (see below) in FRET resulting from the association of labeled binding domains, sequences or polypeptides and their corresponding binding partner(s) in the presence of a protein- or nucleic acid-modifying enzyme.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where $\text{Index}_{Control}$ is the quantitative result (e.g., amount of- or rate of change in fluorescence at a given frequency, rate of molecular rotation, FRET, rate of change in FRET or other index of modification, including, but not limited to, enzyme inhibition or activation) obtained in assays that lack the candidate modulator (in other words, untreated controls), and $\text{Index}_{Sample}$ represents the result of the same measurement in assays containing the candidate modulator. As described below, control measurements are made with a differentially-labeled binding domain, sequence, nucleic acid or polypeptide and its binding partner only and with these molecules plus a protein- or nucleic acid-modifying enzyme which recognizes a site present on them.

Such a calculation is used in either in vitro or in vivo assays performed according to the invention.

D. In vivo Assays of Enzymatic Activity According to the Invention

Reporter Group Protein Modification in Living Cells

Differentially-labeled binding domains, sequences or polypeptides of the invention and their binding partners are delivered to cells, such as smooth muscle cells (DDT1) or ventricular cardiac myocytes as previously described (Riabowol et al., 1988, *Cold Spring Harbor Symposia on Quantitative Biology* 53:85–90). Where the agent to be delivered is a peptide, protein or polypeptide, delivery may be by means of microinjection. Nucleic acids, such as DNA or RNA oligonucleotides may be transfected into tissue culture cells using standard procedures as described in, for example, Sambrook et al., 1989, *Molecular Cloning. A Laboratory Manual*, 2$^{nd}$ Edition, Cold Spring Harbor Laboratory Press, Cold Spring Harbor, N.Y. and Ausubel et al., *Current Protocols in Molecular Biology*, copyright 1987–1994, *Current Protocols*, copyright 1994–1998, John Wiley & Sons, Inc.). Preferably, lipid based reagents are used for transfection of oligonucleotides into cells. Transfected oligonucleotides are preferably (but need not be) phosphorothioate derivatives for increased stability in intracellular environments.

If the transfected nucleic acid or oligonucleotide is labeled with a chemical fluorophore as described above, then its distribution and interactions with other entities within the cell may be monitored. Correspondingly, if the oligonucleotide or transfected nucleic acid interacts with a protein which is itself labeled with a fluorophore, then the protein-nucleic acid interaction can be detected by FRET. The labeled protein may be expressed as a fusion protein in the cell by means of a suitable expression construct.

As an example of such an assay, a CREB-GFP fusion protein is expressed in tissue culture cells and the cells are transfected with a rhodamine labeled CRE oligonucleotide. A PKA regulated interaction between CREB and CRE is detected through quenching of the GFP signal by the binding of the rhodamine labeled oligonucleotide to the fusion protein. The ratio of fluorescence emission from the labeled molecule(s) is measured as described above via a photomultiplier tube, which may be focused on a single cell.

A further example is the activation of a kinase (e.g., PKA by the addition of dibutyryl cAMP or β-adrenergic agonists) and subsequent inhibition by removal of stimulus and by addition of a suitable antagonist (e.g., cAMP antagonist Rp-cAMPS). As described elsewhere herein, an ADP ribosylating enzyme may be stimulated with cholera toxin (G-protein recognition feature) or with brefeldin A.

Heterologous Expression of Peptides

Binding domains, sequences or polypeptides and their binding partners can be produced from the heterologous expression of DNA sequences which encode them or may be chemically synthesized. Biological expression can be in procaryotic or eukaryotic cells using a variety of plasmid vectors capable of instructing heterologous expression. Purification of these products is achieved by destruction of the cells (e.g., French Press) and chromatographic purification of the products. This latter procedure can be simplified by the inclusion of an affinity purification tag at one extreme of the peptide, separated from the peptide by a protease cleavage site if necessary.

Use of Cells or Whole Organisms in Assays of the Invention

When performed using cells, the assays of the invention are broadly applicable to a host cell susceptible to transfection or transformation including, but not limited to, bacteria (both gram-positive and gram-negative), cultured- or explanted plant (including, but not limited to tobacco, arabidopsis, carnation, rice and lentil cells or protoplasts), insect (e.g., cultured Drosophila or moth cell lines) or vertebrate cells (e.g., mammalian cells) and yeast.

Organisms are currently being developed for the expression of agents including DNA, RNA, proteins, non-proteinaceous compounds, and viruses. Such vector microorganisms include bacteria such as Clostridium (Parker et al., 1947, *Proc. Soc. Exp. Biol. Med.* 66:461–465; Fox et al., 1996, *Gene Therapy* 3:173–178; Minton et al., 1995, *FEMS Microbiol. Rev.* 17:357–364), Salmonella (Pawelek et al., 1997, *Cancer Res.* 57:4537–4544; Saltzman et al., 1996, *Cancer Biother. Radiopharm.* 11:145–153; Carrier et al., 1992, *J. Immunol.* 148:1176–1181; Su et al., 1992, *Microbiol. Pathol.* 13:465–476; Chabalgoity et al., 1996, *Infect. Immunol.* 65:2402–2412), Listeria (Schafer et al., 1992, *J. Immunol.* 149:53–59; Pan et al., 1995, *Nature Med.* 1:471–477) and Shigella (Sizemore et al., 1995, *Science* 270:299–302), as well as yeast, mycobacteria, slime molds (members of the taxa Dictyosteliida—such as of the genera Polysphondylium and Dictystelium, e.g., *Dictyostelium discoideum*—and Myxomycetes—e.g., of the genera Physarum and Didymium) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Plant cells useful in expressing polypeptides of use in assays of the invention include, but are not limited to, tobacco (*Nicotiana plumbaginfolia* and *Nicotiana tabacum*), arabidopsis (*Arabidopsis thaliana*), *Aspergillus niger*, *Brassica napus*, *Brassica nigra*, *Datura innoxia*, *Vicia narbonensis*, *Vicia faba*, pea (*Pisum sativum*), cauliflower, carnation and lentil (*Lens culinaris*). Either whole plants, cells or protoplasts may be transfected with a nucleic acid of choice. Methods for plant cell transfection or stable transformation include inoculation with *Agrobacterium tumefaciens* cells carrying the construct of interest (see, among others, Turpen et al., 1993, *J. Virol. Methods* 42:227–239), administration of liposome-associated nucleic acid molecules (Maccarrone et al., 1992, *Biochem. Biophys. Res. Commun.* 186:1417–1422) and microparticle injection (Johnston & Tang, 1993, *Genet. Eng.* (*NY*) 15:225–236), among other methods. A generally useful plant transcriptional control element is the cauliflower mosaic virus (CaMV) 35S promoter (see, for example, Saalbach et al., 1994, *Mol. Gen. Genet.* 242:226–236). Non-limiting examples of nucleic acid vectors useful in plants include pGSGLUC1 (Saalbach et al., 1994, supra), pGA492 (Perez et al., 1989, *Plant Mol. Biol.* 13:365–373), pOCA18 (Olszewski et al., 1988, *Nucleic Acids Res.* 16:10765–10782), the Ti plasmid (Roussell et al., 1988, *Mol. Gen. Genet.* 211:202–209) and pKR612B1 (Balazs et al., 1985, *Gene* 40:343–348).

Mammalian cells are of use in the invention. Such cells include, but are not limited to, neuronal cells (those of both primary explants and of established cell culture lines) cells of the immune system (such as T-cells, B-cells and macrophages), fibroblasts, hematopoietic cells and dendritic cells. Using established technologies, stem cells (e.g., hematopoietic stem cells) may be used for gene transfer after enrichment procedures. Alternatively, unseparated hematopoietic cells and stem cell populations may be made susceptible to DNA uptake. Transfection of hematopoietic stem cells is described in Mannion-Henderson et al., 1995, *Exp. Hematol.* 23:1628; Schiffmann et al., 1995, *Blood* 86:1218; Williams, 1990, *Bone Marrow Transplant* 5:141; Boggs, 1990, *Int. J. Cell Cloning* 8:80; Martensson et al., 1987, *Eur. J. Immuno.* 17:1499; Okabe et al., 1992, *Eur. J. Immunol.* 22:37–43; and Banerji et al., 1983, *Cell* 33:729. Such methods may advantageously be used according to the present invention.

Nucleic Acid Vectors for the Expression of Assay Components of the Invention in Cells or Multicellular Organisms A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient mammal. It is also possible to design a vector that will express the gene of choice in the target cells at a specific time, by using an inducible promoter, which will not direct transcription unless a specific stimulus, such as heat shock, is applied.

A gene encoding a component of the assay system of the invention or a candidate modulator of protein- or nucleic acid- modifying enzyme activity may be transfected into a cell or organism using a viral or non-viral DNA or RNA vector, where non-viral vectors include, but are not limited to, plasmids, linear nucleic acid molecules, artificial chromosomes and episomal vectors. Expression of heterologous genes in mammals has been observed after injection of plasmid DNA into muscle (Wolff J. A. et al, 1990, *Science* 247:1465–1468; Carson D. A. et al., U.S. Pat. No. 5,580,859), thyroid (Sykes et al., 1994, *Human Gene Ther.* 5:837–844), melanoma (Vile et al., 1993, *Cancer Res.* 53:962–967), skin (Hengge et al., 1995, *Nature Genet.* 10:161–166), liver (Hickman et al., 1994, *Human Gene Therapy* 5:1477–1483) and after exposure of airway epithelium (Meyer et al., 1995, *Gene Therapy* 2:450–460).

In addition to vectors of the broad classes described above and gene expression constructs encoding fusion proteins comprising binding domains, sequences or polypeptides fused in-frame with fluorescent proteins as described above (see "Fluorescent resonance energy transfer"), microbial plasmids, such as those of bacteria and yeast, are of use in the invention.

Bacterial Plasmids:

Of the frequently used origins of replication, pBR322 is useful according to the invention, and PUC is preferred. Although not preferred, other plasmids which are useful according to the invention are those which require the presence of plasmid encoded proteins for replication, for example, those comprising pT181, FI, and FI origins of replication.

Examples of origins of replication which are useful in assays of the invention in *E.coli* and *S. typhimurium* include but are not limited to, pHETK (Garapin et al., 1981, *Proc. Natl. Acad. Sci. U.S.A.* 78:815–819), p279 (Talmadge et al., 1980, *Proc. Natl. Acad. Sci. U.S.A.* 77:3369–3373), p5-3 and p21A-2 (both from Pawalek et al., 1997, *Cancer Res.* 57:4537–4544) pMB1 (Bolivar et al., 1977, *Gene* 2:95–113), ColE1 (Kahn et al., 1979, *Methods Enzymol.* 68:268–280), p15A (Chang et al., 1978, *J. Bacteriol.* 134:1141–1156); pSC101 (Stoker et al., 1982, *Gene* 18:335–341); R6K (Kahn et al., 1979, supra); R1 (temperature dependent origin of replication, Uhlin et al, 1983, *Gene* 22:255–265); lambda dv (Jackson et al., 1972, *Proc. Nat. Aca. Sci. U.S.A.* 69:2904–2909); pYA (Nakayama et al., 1988, infra). An example of an origin of replication that is useful in Staphylococcus is pT181 (Scott, 1984, *Microbial Reviews* 48:1–23). Of the above-described origins of replication, pMB1, p15A and ColE1 are preferred because these origins do not require plasmid-encoded proteins for replication.

Yeast Plasmids:

Three Systems are Used for Recombinant Plasmid Expression and Replication in Yeasts:

1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g., as described by Rose et al., 1990, *Methods in Yeast Genetics*, Cold Spring Harbor Laboratory Press, Cold Spring Harbor, N.Y.). The cells are treated with lithium acetate to achieve transformation efficiencies of approximately $10^4$ colony-forming units (transformed cells)/g of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copes per cell; however, this plasmid is both mitotically and meiotically unstable.

3. High-copy-number $2\mu$ circles. These plasmids contain a sequence approximately 1 kb in length, the $2\mu$ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids useful in the invention include the YRp plasmids (based on autonomously-replicating sequences, or ARS) and the YEp plasmids (based on the $2\mu$ circle), of which examples are YEp24 and the YEplac series of plasmids (Gietz & Sugino, 1988, *Gene* 74:527–534). (See Sikorski, "Extrachromsomoal cloning vectors of *Saccharomyces cerevisiae*", in *Plasmids, A Practical Approach*, Ed. K. G. Hardy, IRL Press, 1993; and *Yeast Cloning Vectors and Genes, Current Protocols in Molecular Biology*, Section II, Unit 13.4, Eds., Ausubel et al., 1994.)

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 (PhosphoADP-ribosylanthranilate isomerase, which is a component of the tryptophan biosynthetic pathway).

URA3 (Orotidine-5'-phosphate decarboxylase, which takes part in the uracil biosynthetic pathway).

LEU2 (3-Isopropylmalate dehydrogenase, which is involved with the leucine biosynthetic pathway).

HIS3 (Imidazoleglycerolphosphate dehydratase, or IGP dehydratase).

LYS2 (α-aminoadipate-semialdehyde dehydrogenase, part of the lysine biosynthetic pathway).

Alternatively, the screening system may operate in an intact, living multicellular organism, such as an insect or a mammal. Methods of generating transgenic Drosophila, mice and other organisms, both transiently and stably, are well known in the art; detection of fluorescence resulting from the expression of Green Fluorescent Protein in live Drosophila is well known in the art. One or more gene expression constructs encoding one or more of a labeled binding domain, sequence, nucleic acid or polypeptide, a binding partner therefor, a protein-modifying enzyme and, optionally, a candidate modulator thereof are introduced into the test organism by methods well known in the art (see also below). Sufficient time is allowed to pass after administration of the nucleic acid molecule to allow for gene expression, for binding of binding domains, sequences or polypeptides and their binding partners, and for chromophore maturation, if necessary (e.g., Green Fluorescent Protein matures over a period of approximately 2 hours prior to fluorescence) before FRET is measured. A reaction component (particularly a candidate modulator of enzyme function) which is not administered as a nucleic acid molecule may be delivered by a method selected from those described below.

Dosage and Administration of a Labeled Binding Domain. Sequence, Nucleic Acid or Polypeptide. a Binding Partner and Protein- or Nucleic Acid- modifying Enzyme or Candidate Modulator Thereof for Use in an In vivo Assay of the Invention i. Dosage For example, the amount of each labeled binding domain or binding partner therefor must fall within the detection limits of the fluorescence-measuring device employed. The amount of an enzyme or candidate modulator thereof will typically be in the range of about 1 $\mu$g –100 mg/kg body weight. Where the candidate modulator is a peptide or polypeptide, it is typically administered in the range of about 100–500 $\mu$g/ml per dose. A single dose of a candidate modulator, or multiple doses of such a substance, daily, weekly, or intermittently, is contemplated according to the invention.

A candidate modulator is tested in a concentration range that depends upon the molecular weight of the molecule and the type of assay. For example, for inhibition of protein/DNA complex formation or transcription initiation (depending upon the level at which the candidate modulator is thought or intended to modulate the activity of a protein or nucleic acid modifying enzyme according to the invention), small molecules (as defined above) may be tested in a concentration range of 1 pg–100 $\mu$g/ml, preferably at about 100 pg–10 ng/ml; large molecules, e.g., peptides, may be tested in the range of 10 ng–100 $\mu$g/ml, preferably 100 ng–10 $\mu$g/ml.

Generally, nucleic acid molecules are administered in a manner compatible with the dosage formulation, and in such amount as will be effective. In the case of a recombinant nucleic acid encoding a natural or engineered binding domain and/or binding partner therefor, such an amount should be sufficient to result in production of a detectable amount of the labeled protein or peptide, as discussed above. In the case of a protein or nucleic acid modifying enzyme, the amount produced by expression of a nucleic acid molecule should be sufficient to ensure that at least 10% of binding domains will undergo modification if they comprise a target site recognized by the enzyme being assayed. Lastly, the amount of a nucleic acid encoding a candidate modulator of a protein or nucleic acid modifying enzyme of the invention must be sufficient to ensure production of an amount of the candidate modulator which can, if effective, produce a change of at least 10% in the effect of the target protein or nucleic acid modifying enzyme on FRET resulting from binding of a binding domain to its binding partner or, if administered to a patient, an amount which is prophylactically and/or therapeutically effective.

When the end product (e.g., an antisense RNA molecule or ribozyme) is administered directly, the dosage to be administered is directly proportional to the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5- to 1 $\mu$g, or 1–10 $\mu$g, or optionally 10–100 $\mu$g of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

If no effect (e.g., of a modifying enzyme or an inhibitor thereof) is seen within four orders of magnitude in either direction of the starting dosage, it is likely that an enzyme does not recognize the target site of the binding domain according to the invention, or that the candidate modulator thereof is not of use according to the invention. It is critical to note that when high dosages are used, the concentration must be kept below harmful levels, which may be known if an enzyme or candidate modulator is a drug that is approved for clinical use. Such a dosage should be one (or, preferably, two or more) orders of magnitude below the $LD_{50}$ value that is known for a laboratory mammal, and preferably below concentrations that are documented as producing serious, if non-lethal, side effects.

Components of screening assays of the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of labeled polypeptides comprising a binding domain, sequence, nucleic acid polypeptide or a binding partner therefor, a methylase, demethylase, protein kinase or phosphatase or a candidate modulator as described herein may be either localized or systemic.

Localized Administration:

Localized administration of a component of an assay of the invention is preferably by via injection or by means of a drip device, drug pump or drig-saturated solid matrix from which the nucleic acid can diffuse implanted at the target site. When a tissue that is the target of delivery according to the invention is on a surface of an organism, topical administration of a pharmaceutical composition is possible.

Compositions comprising a composition of- or of use in the invention which are suitable for topical administration can take one of several physical forms, as summarized below:

(i) A liquid, such as a tincture or lotion, which may be applied by pouring, dropping or "painting" (i.e., spreading manually or with a brush or other applicator such as a spatula) or injection.

(ii) An ointment or cream, which may be spread either manually or with a brush or other applicator (e.g., a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which maybe dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a candidate modulator of a protein or nucleic acid modifying enzyme, such as a methylase, demethylase, kinase or phosphatase is to be delivered for assay (or, if found effective, for therapeutic use) is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.* 84:1349–1354).

Systemic Administration:

Systemic administration of a protein, nucleic acid or other agent according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced protein, nucleic acid or other material or may, instead, comprise cells that produce and secrete a binding domain and/or a binding partner therefor, modifying enzyme or candidate modulator thereof. Note that injection may be performed either by conventional means (i.e., using a hypodermic needle) or by hypospray (see Clarke & Woodland, 1975, *Rheumatol. Rehabil.* 14:47–49). Components of assays of the invention can be given in a single- or multiple dose.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

Use of Binding Partners Identified by Phase Display in an Assay of the Invention The component polypeptides of a "binding pair" comprising an binding domain and its binding partner, such as those identified through phage display as above, are expressed and purified by molecular and biochemical known to one of ordinary skill in the art. At least one of the binding domain and the binding partner is labeled with a detectable label, as described above. The binding domain is contacted with the binding partner in a buffer or other medium which permits modification-dependent protein:nucleic acid binding (binding that occurs specifically when the site for enzymatic modification is in one modification state but not the other). Methods by which to assess protein:nucleic acid binding (e.g., FRET, fluorescence correlation spectroscopy, monomer:excimer fluorescence, fluorescence anisotropy, determination of mass or monitoring of enzymatic activity) are performed, both in the presence and absence of modifying enzyme, candidate modifying enzyme (i.e., an enzyme of unknown function) or a biological sample whose enzymatic activity is assayed according to the methods of the invention.

According to one useful technique, the binding domain, which is not labeled with a detectable label, is immobilized and then contacted with the binding partner, where the partner is still attached to a phage particle from the phage display procedure. Interactions between the domain and the binding partner are monitored through the partner protein still attached to the phage particle (surface plasmon resonance). Alternatively, FCS is used if the pure protein component is fluorescent, rather than immobilized. A difference of at least 10% in surface plasmon resonance or fluorescence emission respectively observed in the presence of the modifying enzyme, candidate modifying enzyme or biological sample relative to that observed in its absence indicates that the enzyme or sample being tested has protein- or nucleic acid-modifying activity.

EXAMPLES

Example 1

The Binding of CREB Protein to the CRE DNA Binding Site in a Phosphorylation Dependent Manner The assay involves the following components: CREB protein (accession number M27691), CRE binding site (double stranded DNA, of sequence, CCTCCTTGGCTGACGTCAGAGAGAGAGT), Protein kinase A, PKA (Sigma) and glycogen synthase kinase-3, GSK-3 (New England Biolabs).

Specific DNA sequences known as cyclic-AMP response elements (CREs) are found within the promoters of many cAMP responsive genes. Such sequences bind specific proteins including the CREB family of transcription factors (Bullock & Hebener, 1998, *Biochemistry* 37:3795–3809). CREB/CRE binding has been shown to be a phosphorylation dependent event, with phosphorylation at ser119 by PKA enhancing binding and subsequent phosphorylation by GSK-3 at ser115 disrupting binding.

The assay may be carried out in 2 possible formats.

i) A solution phase fluorescence resonance energy transfer (FRET) reaction.

ii) An immobilized reaction, monitoring the. retention of labeled protein/DNA.

i) A Solution Phase FRET Reaction

The assay is,

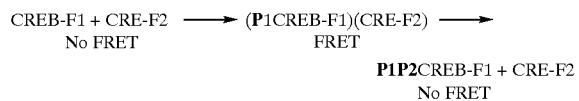

F1 is the donor fluorophore and F2 the acceptor fluorophore. P1 denotes the addition of a phosphate group to ser119 by PKA, and P2 the addition of a second phosphate group at ser115 by GSK-3.

The DNA binding domain of CREB is close to the C-terminus of the protein and thus the C-terminus may be the ideal position for F1. However, if this position interferes with binding the N-terminus is also a yalid labeling location. The F2 label may be positioned 5' or 3' on the DNA sequence.

ii) An Immobilized Reaction, Monitoring the Retention of Labeled Protein/DNA

The assay is,

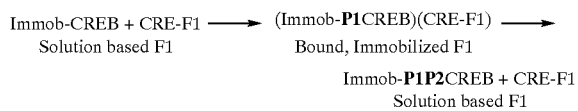

F1 is the fluorophore. P1 denotes the addition of a phosphate group to ser119 by PKA, and P2 the addition of a second phosphate group at ser115 by GSK-3. Immob- represents immobilization to a surface such as a 96 well plate.

Immobilization of CREB may be achieved via binding of an N-terminal or C-terminal affinity tag to an appropriately coated surface, e.g., poly His tag to a $Ni^{2+}$ coated plate.

Alternatively,

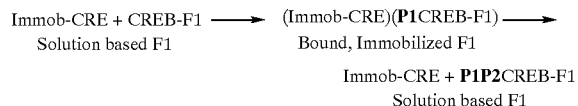

F1 is the fluorophore. P1 denotes the addition of a phosphate group to ser119 by PKA, and P2 the addition of a second phosphate group at ser115 by GSK-3. Immob- represents immobilization to a surface such as a 96 well plate.

Immobilization of CRE may be achieved via binding of a 5' or 3' affinity tag to an appropriately coated surface, e.g., Biotin tag to a streptavidin coated plate.

Example 2

The Binding of OmpR to the OmpF Regulatory Region of DNA

The assay involves the following components: OmpR (accession number P03025). EnvZ histidine kinase (accession number P02933), amino acids 105–450, cloned without its N-terminal transmembrane domain in order to retain soluble enzyme activity, OmpF promoter region, 76 base pairs, consisting of the F1, F2 and F3 OmpR binding sites (Huang et al., 1997, *Proceedings of the National Academy of Sciences USA*, 94:2828–2832).

Multiple copies of OmpR may bind across the entire promoter region (f1–f3) or to individual components of the binding region, e.g., to f2 or f3 only or to a f2–f3 fragment (Head et al., 1998, *J. Mol. Biol.* 281:857–870). The f2f3ompF region (double stranded DNA, of sequence, TTTCTTTTTGAAACCAAATCTTTATCTTTGTAGCAC-TTTC) is used in the following examples.

OmpR consists of an N-terminal phosphorylation domain and a C-terminal DNA binding domain (Kato et al., 1998, *FEBS Lett.* 249:168–172). OmpR is a prokaryotic protein and regulates the production of outer membrane proteins (OMPs) such as ompF and ompC in *E.coli* (Head et al., 1998, *J. Mol. Biol.* 281:857–870) and a type III secretion system in Salmonella (Lee et al., 2000, *Journal of Bacteriology* 182:771–781). Phosphorylation of OmpR at asp55 by the histidine kinase, EnvZ, stimulates the cooperative DNA binding properties of this protein to the ompF promoter (Huang et al., 1997, *Proceedings of the National Academy of Sciences USA* 94:2828–2832).

The assay may be carried out in 2 possible formats.

i) A solution phase fluorescence resonance energy transfer (FRET) reaction.

ii) An immobilized reaction, monitoring the retention of labeled protein/DNA.

i) A Solution Phase Fluorescence Resonance Energy Transfer (FRET) Reaction

A solution phase FRET assay is carried out as described below. As noted above, multiple copies (i.e., 2, 3, 4, 5 or more molecules) of OmpR protein may bind to the OmpF promoter. The following reactions may therefore take place.

A. Binding by One Molecule of OmpR

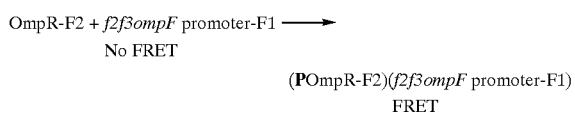

B. Binding by Multiple Molecules of OmpR

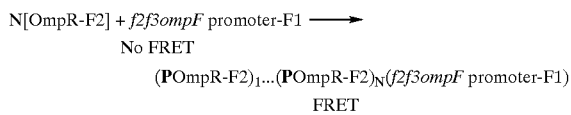

F1 is the donor fluorophore and F2 the acceptor fluorophore. P denotes the addition to OmpR of a phosphate group at asp55 of an OmpR molecule by EnvZ. f2f3ompF represents the f2–f3 region of the ompF promoter. Other regions or combinations of regions of this promoter may be used. $(POmpR-F2)_1 \ldots (POmpR-F2)_N$(f2f3ompF promoter-F1) represents a complex of multiple copies of phosphorylated OmpR and OmpF. The donor fluorophore, F1, could be located on either the N or C terminus of an OmpR molecule. The acceptor fluorophore, F2, could be located on either the 5' or 3' terminus of the DNA.

As can be seen above, the assay detects, by the presence of FRET, binding by one molecule of labeled OmpR to the ompF promoter. Furthermore, the assay is capable of detecting binding by multiple copies of labeled OmpR to the ompF promoter.

ii) An Immobilized Reaction, Monitoring the Retention of Labeled Protein/DNA

An assay is described in which the activity of EnvZ is monitored by detecting the binding of immobilized OmpR protein or OmpF promoter, by the presence or absence of FRET.

An assay utilizing immobilized OmpR is set up as follows:

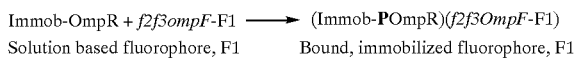

F1 is the fluorophore. P denotes the addition of a phosphate group to asp55 of OmpR by EnvZ. Immob- represents immobilization to a surface such as a 96 well plate. Immobilization of OmpR may be achieved via binding of an N-terminal or C-terminal affinity tag to an appropriately coated surface, e.g., poly His tag to a $Ni^{2+}$ coated 96 well plate.

Alternatively, the ompF promoter may be immobilized:

Immob-f2f3ompF promoter + OmpR-F1 ⟶
Solution based fluorophore, F1
                    (Immob-f2f3ompF promoter)(POmpR-F1)
                    Bound, immobilized fluorophore, F1

F1 is the fluorophore. P denotes the addition to OmpR of a phosphate group at asp55 by EnvZ. Immob- represents immobilization to a surface such as a 96 well plate. Immobilization f2f3ompF promoter may be achieved via binding of a 5' or 3' affinity tag to an appropriately coated surface, e.g., Biotin tag to a streptavidin coated 96 well plate.

As noted above, more than one molecule of OmpR may bind to OmpF. Thus, an assay in which OmpF is immobilized is particularly suitable for detection of binding by either one or multiple molecules of OmpR protein to OmpF. Thus, the following reaction results in FRET, and is detectable in this assay:

Immob-f2f3ompF promoter + N[OmpR-F1] ⟶
Solution based fluorophore, F1
                  (Immob-f2f3ompF promoter)(Pomp R-F1)$_1$ ... (PompF-f1)$_N$
                  Bound, immobilized fluorophore, F1

Example 3

Binding of p53 to the p53 Response Element DNA

The assay involves the following components: p53 (accession number P04637), p53 response element DNA (WAF1/p21/Cip1 binding site) (5'-AATTCTCGAGGAACATGTCCCAACATGTTGCTCGAG-3'), and cyclin A/Cdk2 or cyclin B/Cdc2 kinases.

p53 has a central role in cell regulation. It has specific interactions with genes that control the cell cycle and apoptosis. Wang & Prives (1995, Nature 376:89–91) have demonstrated phosphorylation dependent p53 binding to specific sequences of DNA. Phosphorylation of p53 by cyclin A/Cdk2 or cyclin B/Cdc2 kinases increases the binding to the WAF1/p21/Cip1 binding site 10–15 fold.

The assay may be carried out in 2 possible formats.
i) A solution phase fluorescence resonance energy transfer (FRET) reaction.
ii) An immobilized reaction, monitoring the retention of labeled protein/DNA.
i) A Solution Phase Fluorescence Resonance Energy Transfer (FRET) Reaction
The assay is, p53-F1 + binding site-F2 ⟶ (Pp53-F1)(binding site-F2)
    No FRET                             FRET F1 is the donor fluorophore and F2 the acceptor fluorophore. P denotes, the addition of a phosphate group to ser315 of p53 by cyclin A/Cdk2 or cyclin B/Cdc2.

The donor fluorophore, F1, can be located on either the N or C terminus of p53 although a C-terminal label may interfere with the C-terminal DNA binding domain of p53. The acceptor fluorophore, F2, could be located on either the 5' or 3' end of the DNA.

ii) An Immobilized Reaction, Monitoring the Retention of Labeled Protein/DNA

The assay is,

Immob-p53 + binding site-F1 ⟶ (Immob-Pp53)(binding site-F1)
Solution based fluorophore, F1     Bound, immobilized fluorophore, F1

F1 is the fluorophore. P denotes the addition of a phosphate group to ser315 of p53 by cyclin A/Cdk2 or cyclin B/Cdc2. Immob- represents immobilization to a surface such as a 96 well plate.

Immobilization of p53 may be achieved via binding of an N-terminal or C-terminal affinity tag to an appropriately coated surface, e.g., poly His tag to a Ni$^{2+}$ coated plate. An N-terminal tag may be preferential due to the C-terminal location of the DNA binding site in p53.

Alternatively,

Immob-binding site + p53-F1 ⟶ (Immob-binding site)(Pp53-F1)
Solution based fluorophore, F1     Bound, immobilized fluorophore, F1

F1 is the fluorophore. P denotes the addition of a phosphate group to ser315 of p53 by cyclin A/Cdk2 or cyclin B/Cdc2. Immob- represents immobilization to a surface such as a 96 well plate.

Immobilization of the binding site may be achieved via binding of a 5' or 3' affinity tag to an appropriately coated surface, e.g., Biotin tag to a streptavidin coated plate.

Example 4

Phosphorylation Dependent Binding of the HIV-1 H6Rev Protein to Stem-loop IIB RNA The assay involves the following components: H6Rev protein (accession number P04325), Stem-loop IIB RNA (Fouts et al., 1997, Biochemistry 36:13256–13262) and PKC or Heart Muscle Kinase (HMK).

The Rev protein from HIV type I is an essential post-transcriptional regulator of virion gene expression. Phosphorylation of H6Rev by either PKC or HMK enables it to bind 7 fold more tightly to stem-loop IIB RNA than unphosphorylated H6Rev (Fouts et al., 1997, Biochemistry 36:13256–13262).

The assay may be carried out in 2 possible formats.
i) A solution phase fluorescence resonance energy transfer (FRET) reaction.
ii) An immobilized reaction, monitoring the retention of labeled protein/DNA.
i) A Solution Phase Fluorescence Resonance Energy Transfer (FRET) Reaction
The assay is, H6Rev-F1 + Stem-loop IIB RNA-F2 ⟶
           No FRET
                        (PH6Rev-F1)(Stem-loop IIB RNA-F2)
                                  FRET F1 is the donor fluorophore and F2 the acceptor fluorophore. P denotes the addition of a phosphate group to Ser54/ser56 of PH6Rev by PKC or HMK.

The donor fluorophore, F1, could be located on either the N or C terminus of H6Rev. The acceptor fluorophore, F2 may be located at either the 5' or 3' terminus of the RNA.

ii) An Immobilized Reaction, Monitoring the Retention of Labeled Protein/RNA

The assay is,

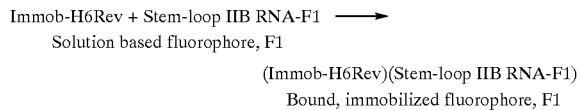

Solution based fluorophore, F1

(Immob-H6Rev)(Stem-loop IIB RNA-F1)
Bound, immobilized fluorophore, F1

F1 is the fluorophore. P denotes the addition of a phosphate group to ser54/ser56 of PH6Rev by PKC or HMK. Immob- represents immobilization to a surface such as a 96 well plate.

Immobilization of H6Rev may be achieved via binding of an N or C-terminal affinity tag to an appropriately coated surface, e.g., Poly His tag to a $Ni^{2+}$ coated 96 well plate.

Alternatively,

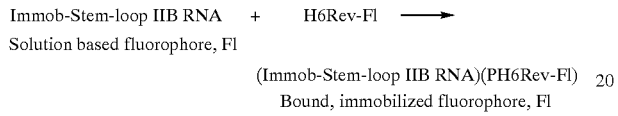

Solution based fluorophore, Fl (Immob-Stem-loop IIB RNA)(PH6Rev-Fl)
Bound, immobilized fluorophore, Fl F1 is the fluorophore. P denotes the addition of a phosphate group to ser54/ser56 of PH6Rev by PKC or HMK. Immob- represents immobilization to a surface such as a 96 well plate.

Immobilization of Stem-loop IIB RNA may be achieved via binding of a 3' or 5' affinity tag to an appropriately coated surface, e.g., Biotin tag to a streptavidin coated 96 well plate.

Use

The invention is useful in monitoring the activity of a protein- or nucleic acid-modifying enzyme, whether the protein is isolated, partially-purified, present in a crude preparation or present in a living cell. The invention is further useful in assaying a cell or cell extract for the presence- or level of activity of a protein or nucleic acid modifying enzyme. The invention is additionally useful in assaying the activity of naturally-occurring (mutant) or non-natural (engineered) isoforms of known protein or nucleic acid modifying enzymes or, instead, that of novel (natural or non-natural) enzymes. The invention is of use in assaying the efficacy of candidate modulators of the activity of a protein or nucleic acid modifying enzyme in inhibiting or enhancing the activity of that enzyme; moreover, is useful to screen potential therapeutic drugs for activity against cloned and/or purified enzymes that may have important clinical pathogenicities when mutated. The invention is further of use in the screening of candidate bioactive agents (e.g., drugs) for side effects, whereby the ability of such an agent to modulate the activity of a protein or nucleic acid modifying enzyme may be indicative a propensity toward provoking unintended side-effects to a therapeutic or other regimen in which that agent might be employed.

Other Embodiments

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for monitoring the activity of an enzyme, the method comprising the steps of:
   (a) providing a binding domain which includes a site for enzymatic modification;
   (b) providing a binding partner which binds to the binding domain in a manner which is dependent upon modification of the site;
   (c) contacting the binding domain with the enzyme; and
   (d) detecting binding of the binding domain to the binding partner as an indication of the activity of the enzyme;
   wherein one of said binding domain and said binding partner comprises a polypeptide and the other of said binding domain and said binding partner comprises a nucleic acid; and wherein said binding domain comprises a polypeptide and said site comprises a sequence which directs modification by at least one of the following enzymes: a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, and an NAD: Arginine ADP ribosyltransferase.

2. A method for monitoring the activity of an enzyme, the method comprising the steps of:
   (a) providing a binding domain which includes a site for enzymatic modification;
   (b) providing a binding partner which dissociates from the binding domain in a manner which is dependent upon modification of the site;
   (c) contacting the binding domain with the enzyme; and
   (d) detecting dissociation of the binding domain from the binding partner as an indication of the activity of the enzyme;
   wherein one of said binding domain and said binding partner comprises a polypeptide and the other of said binding domain and said binding partner comprises a nucleic acid; and
   wherein said binding domain comprises a polypeptide and said site comprises a sequence which directs modification by at least one of the following enzymes: a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, and an NAD: Arginine ADP ribosyltransferase.

3. The method of claim 1 or 2, wherein said site permits addition of a chemical moiety, and the addition prevents binding of said binding domain to said binding partner.

4. The method of claim 3, wherein said chemical moiety is selected from the group consisting of: a ubiquitin moiety, a glycosyl moiety, an ADP-ribosyl moiety, a fatty acyl moiety, a sentrin moiety, and a methyl group.

5. The method of claim 1 or 2, wherein said site permits addition of a chemical moiety, and said addition promotes binding of said binding domain to said binding partner.

6. The method of claim 5, wherein said chemical moiety is selected from the group consisting of: a ubiquitin moiety, a glycosyl moiety, an ADP-ribosyl moiety, a fatty acyl moiety, a sentrin moiety, and a methyl group.

7. The method of claim 1 or 2, wherein said site permits removal of a chemical moiety, and said removal prevents binding of said binding domain to said binding partner.

8. The method of claim 7, wherein said chemical moiety is selected from the group consisting of: a ubiquitin moiety, a glycosyl moiety, an ADP-ribosyl moiety, a fatty acyl moiety, a sentrin moiety, and a methyl group.

9. The method of claim 7, wherein said detection step comprises detection of a change in signal emission by the detectable label.

10. The method of claim 1 to 2 wherein said site permits removal of a chemical moiety, and said removal promotes binding of said binding domain to said binding partner.

11. The method of claim 10, wherein said chemical moiety is selected from the group consisting of: a ubiquitin moiety, a glycosyl moiety, an ADP-ribosyl moiety, a fatty acyl moiety, a sentrin moiety, and a methyl group.

12. The method of claim 1 or 2, wherein at least one of said binding domain and said binding partner comprises a detectable label.

13. The method of claim 12, wherein said method further comprises exciting said detectable label and monitoring fluorescence emission.

14. The method of claim 12, wherein said detectable label emits light.

15. The method of claim 14, wherein said detection step comprises detection of a change in signal emission by said detectable label.

16. The method of claim 14, wherein said method further comprises exciting said detectable label and monitoring fluorescence emission.

17. The method of claim 14, wherein said light is emitted as a result of fluorescence.

18. The method of claim 17, wherein said detection step comprises detection of a change in signal emission by said detectable label.

19. The method of claim 17, wherein said method further comprises exciting said detectable label and monitoring fluorescence emission.

20. The method of claim 1 or 2, wherein one of said binding domain and said binding partner comprises a quencher for the detectable label.

21. The method of claim 20, wherein said detection step comprises detection of a change in signal emission by said detectable label.

22. The method of claim 20, wherein said method further comprises exciting said detectable label and monitoring fluorescence emission.

23. The method of claim 1 or 2, wherein said method further comprises the step, prior to or after the detecting step, of contacting said binding domain and said binding partner with an agent which modulates the activity of said enzyme.

24. A method of screening for a candidate modulator of enzymatic activity of at least one of the following enzymes: a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD: Arginine ADP ribosyltransferase, said method comprising:

(a) contacting a binding domain comprising a polypeptide, a binding partner therefor comprising a nucleic acid, and an enzyme with a candidate modulator of the enzyme, wherein said binding domain includes a site for enzymatic modification and binds said binding partner in a manner that is dependent upon modification of said site by said enzyme, and wherein at least one of said binding domain and said binding partner comprises a detectable label, and (b) monitoring said binding of said binding domain to said binding partner, wherein binding or dissociation of said binding domain and said binding partner as a result of said contacting is indicative of modulation of enzyme activity by said candidate modulator of said enzyme.

25. A method of screening for a candidate modulator of enzymatic activity of a methylase or a demethylase, said method comprising:

(a) contacting a binding domain comprising a nucleic acid, a binding partner therefor comprising a polypeptide, and an enzyme with a candidate modulator of the enzyme, wherein said binding domain includes a site for enzymatic modification and binds said binding partner in a manner that is dependent upon modification of said site by said enzyme, and wherein at least one of said binding domain and said binding partner comprises a detectable label, and (b) monitoring said binding of said binding domain to said binding partner, wherein binding or dissociation of said binding domain and said binding partner as a result of said contacting is indicative of modulation of enzyme activity by said candidate modulator of said enzyme.

26. The method of claim 24 or 25, wherein said detectable label emits light.

27. The method of claim 26, wherein said light is emitted as a result of fluorescence.

28. The method of claim 24 or 25, wherein said monitoring comprises measuring a change in energy transfer between a label present on said binding domain and a label present on said binding partner.

29. A method of screening for a candidate modulator of enzymatic activity of at least one of the following enzymes: a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD: Arginine ADP ribosyltransferase, said method comprising:

(a) providing a binding domain which includes a site for enzymatic modification;

(b) providing a binding partner which binds to the binding domain in a manner which is dependent upon modification of the site;

(c) contacting an assay system with a candidate modulator of enzymatic activity of an enzyme, and (d) monitoring binding of a binding domain comprising a polypeptide and a binding partner therefor comprising a nucleic acid in the assay system, wherein said binding domain includes a site for enzymatic modification and binds said binding partner in a manner that is dependent upon modification of said site by at least one enzyme in the assay system, wherein at least one of said binding domain and said binding partner comprises a detectable label, and wherein binding or dissociation of said binding domain and said binding partner as a result of said contacting is indicative of modulation of enzyme activity by said candidate modulator of said enzyme.

30. A method of screening for a candidate modulator of enzymatic activity of a methylase or a demethylase, said method comprising:

(a) contacting an assay system with a candidate modulator of enzymatic activity of an enzyme, and (b) monitoring binding of a binding domain comprising a nucleic acid and a binding partner therefor comprising a polypeptide in the assay system, wherein said binding domain includes a site for enzymatic modification and binds said binding partner in a manner that is dependent upon modification of said site by at least one enzyme in said assay system, wherein at least one of said binding domain and said binding partner comprises a detectable label, and wherein binding or dissociation of said binding domain and said binding partner as a result of said contacting is indicative of modulation of enzyme activity by said candidate modulator of said enzyme.

31. The method of claim 1, 2, 24, 25, 29 or 30, wherein said method comprises realtime observation of association of binding domain and said partner.

32. A method for monitoring the activity of a methylase or a demethylase, the method comprising the steps of:
   (a) providing a binding domain which includes a site for enzymatic modification;
   (b) providing a binding partner which binds to the binding domain in a manner which is dependent upon modification of the site;
   (c) contacting the binding domain with the enzyme; and
   (d) detecting binding of the binding domain to the binding partner as an indication of the activity of the enzyme;
   wherein one of said binding domain and said binding partner comprises a polypeptide and the other of said binding domain and said binding partner comprises a nucleic acid; and
   wherein said binding domain comprises a nucleic acid, and said site comprises a sequence which directs modification by one or more of a methylase and a demethylase.

33. A method for monitoring the activity of a methylase or a demethylase, the method comprising the steps of:
   (a) providing a binding domain which includes a site for enzymatic modification;
   (b) providing a binding partner which dissociates from the binding domain in a manner which is dependent upon modification of the site;
   (c) contacting the binding domain with the enzyme; and
   (d) detecting dissociation of the binding domain from the binding partner as an indication of the activity the enzyme;
   wherein one of said binding domain and said binding partner comprises a polypeptide and the other of said binding domain and said binding partner comprises a nucleic acid; and
   wherein aid binding domain comprises a nucleic acid, and said site comprises a sequence which directs modification by one or more of a methylase and a demethylase.

34. The method of claim 32 or 33, wherein said site permits addition of a chemical moiety, and the addition prevents binding of said binding domain to said binding partner.

35. The method of claim 32 or 33, wherein said site permits removal of a chemical moiety, and said removal prevents binding of said binding domain to said binding partner.

36. The method of claim 32 or 33, wherein at least one of said binding domain and said binding partner comprises a detectable label.

37. The method of claim 36, wherein said detectable label emits light.

38. The method of claim 37, wherein said light is emitted as a result of fluorescence.

39. The method of claim 32 or 33, wherein one of said binding domain and said binding partner comprises a quencher for the detectable label.

40. The method of claim 32 or 33, wherein said detection step comprises detection of a change in signal emission by the detectable label.

41. The method of claim 32 or 33, wherein said method further comprises the step, prior to or after the detecting step, of contacting said binding domain and said binding partner with an agent which modulates the activity of said enzyme.

42. A method for monitoring the activity of an enzyme, the method comprising the steps of:
   (a) providing a binding domain which includes a site for enzymatic modification;
   (b) providing a binding partner which binds to the binding domain in a manner which is dependent upon modification of the site;
   (c) contacting the binding domain with the enzyme; and
   (d) detecting binding of the binding domain to the binding partner as an indication of the activity of the enzyme;
   wherein one of said binding domain and said binding partner comprises a polypeptide and the other of said binding domain and said binding partner comprises a nucleic acid;
   wherein said binding domain comprises a polypeptide and said site and said site comprises a sequence which directs modification by at least one of the following enzymes: a kinase or a phosphatase;
   wherein at least one of said binding domain and said binding partner comprises a detectable label; and
   wherein said detection step comprises detection of a change in signal emission by the detectable label.

43. A method for monitoring the activity of an enzyme, the method comprising the steps of:
   (a) providing a binding domain which includes a site for enzymatic modification;
   (b) providing a binding partner which binds to the binding domain in a manner which is dependent upon modification of the site;
   (c) contacting the binding domain with the enzyme; and
   (d) detecting binding of the binding domain to the binding partner as an indication of the activity of the enzyme;
   wherein one of said binding domain and said binding partner comprises a polypeptide and the other of said binding domain and said binding partner comprises a nucleic acid;
   wherein said binding domain comprises a polypeptide and said site and said site comprises a sequence which directs modification by at least one of the following enzymes: a kinase or a phosphatase;
   wherein at least one of said binding domain and said binding partner comprises a detectable label; and
   wherein said detection step comprises detection of a change in signal emission by the detectable label.

44. A method according to claim 42 or 43, wherein said site comprises a sequence which directs modification by an enzyme selected from the group consisting of: protein kinase A (PKA), glycogen synthase kinase-3 (GSK-3), casein kinase II (CMI), Cdc2 kinase, cyclin E, cdk2, cyclin A, cdk2, cyclin B, cdc2, EnvZ, protein kinase-C (PKC) and heart muscle kinase (HMX).

45. The method of claim 42 or 43, wherein:
   (a) said binding domain comprises a CREB/ATF polypeptide or a fragment thereof and said binding partner comprises a GRE binding site or a fragment thereof;
   (b) said binding domain comprises a p53 polypeptide or a fragment thereof and said binding partner comprises a p53 response element DNA or a fragment thereof;
   (c) said binding domain comprises an OmpR polypeptide or a fragment thereof and said binding partner comprises an OmpF promoter or a fragment thereof; or (d) said binding domain comprises a HIV type-I Rev polypeptide or a fragment thereof and said binding partner comprises a stem-loop IIB RNA.

46. The method of claim 42 or 43, wherein said site permits addition of a phosphate moiety, and the addition prevents binding of said binding domain to said binding partner.

47. The method of claim 42 or 43, wherein said site permits addition of a phosphate moiety, and said addition promotes binding of said binding domain to said binding partner.

48. The method of claim 42 or 43, wherein said site permits removal of a phosphate moiety, and said removal prevents binding of said binding domain to said binding partner.

49. The method of claim 42 or 43 wherein said site permits removal of a phosphate moiety, and said removal promotes binding of said binding domain to said binding partner.

50. The method of claim 42 or 43, wherein said detectable label emits light.

51. The method of claim 42 or 43, wherein said light is emitted as a result of fluorescence.

52. The method of claim 42 or 43, wherein one of said binding domain and said binding partner comprises a quencher for the detectable label.

53. The method of claim 42 or 43 wherein said method further comprises exciting said detectable label and monitoring fluorescence emission.

54. The method of claim 42 or 43, wherein said method further comprises the step, prior to or after the detection step, of contacting said binding domain and said binding partner with an agent which modulates the activity of said enzyme.

55. A method of screening for a candidate modulator of enzymatic activity of at least one of the following enzymes: a kinase, and a phosphatase, said method comprising:
   (a) contacting a binding domain comprising a polypeptide, a binding partner therefor comprising a nucleic acid, and an enzyme with a candidate modulator of the enzyme, wherein said binding domain includes a site for enzymatic modification and binds said binding partner in a manner that is dependent upon modification of said site by said enzyme, and wherein at least one of said binding domain and said binding partner comprises a detectable label, and
   (b) monitoring said binding of said binding domain to said binding partner, wherein binding or dissociation of said binding domain and said binding partner as a result of said contacting is indicative of modulation of enzyme activity by said candidate modulator of said enzyme; and
   (c) detecting binding of the binding domain to the binding partner as an indication of the activity of the enzyme
   wherein said detection step comprises detection of a change in signal emission by the detectable label.

56. The method of claim 55, wherein said detectable label emits light.

57. The method of claim 55, wherein said light is emitted as a result of fluorescence.

58. The method of claim 55, wherein said monitoring comprises measuring a change in energy transfer between a label present on said binding domain and a label present on said binding partner.

59. A method of screening for a candidate modulator of enzymatic activity of at least one of the following enzymes: a kinase and a phosphatase, said method comprising:
   (a) providing a binding domain which includes a site for enzymatic modification;
   (b) providing a binding partner which binds to the binding domain in a manner which is dependent upon modification of the site;
   (c) contacting an assay system with a candidate modulator of enzymatic activity of an enzyme, and
   (d) monitoring binding of a binding domain comprising a polypeptide and a binding partner therefor comprising a nucleic acid in the assay system using fluorescence resonance energy transfer, wherein said binding domain includes a site for enzymatic modification and binds said binding partner in a manner that is dependent upon modification of said site by at least one enzyme in the assay system, wherein at least one of said binding domain and said binding partner comprises a detectable label, wherein binding or dissociation of said binding domain and said binding partner as a result of said contacting is indicative of modulation of enzyme activity by said candidate modulator of said enzyme; and
   (e) detecting binding of the binding domain to the binding partner as an indicator of the activity of the enzyme;
   wherein said detection step comprises detection of a change in signal emission by the detectable label.

60. The method of claim 55 or 59, wherein said detectable label emits light.

* * * * *